(12) United States Patent
deBoer et al.

(10) Patent No.: US 6,446,486 B1
(45) Date of Patent: Sep. 10, 2002

(54) MICROMACHINE FRICTION TEST APPARATUS

(75) Inventors: Maarten P. deBoer; James M. Redmond, both of Albuquerque; Terry A. Michalske, Cedar Crest, all of NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/299,804

(22) Filed: Apr. 26, 1999

(51) Int. Cl.⁷ .............................................. G01N 3/56
(52) U.S. Cl. .......................................................... 73/9
(58) Field of Search .................................... 73/7, 9, 10

(56) References Cited

U.S. PATENT DOCUMENTS

| | | | | |
|---|---|---|---|---|
| 4,791,807 A | * | 12/1988 | Oechsle | 73/78 |
| 5,115,664 A | * | 5/1992 | Hegde et al. | 73/9 |
| 5,553,487 A | * | 9/1996 | Elings | 73/9 |
| 5,859,357 A | * | 1/1999 | Kameyama et al. | 73/9 |

OTHER PUBLICATIONS

M.G. Lim, J.C. Chang, D.P. Schultz, R.T. Howe and R.M. White, "Polysilicon Microstructures to Characterize Static Friction," *Proceedings of the IEEE MEMS Workshop*, Feb. 11–14, 1990, pp. 82–88.

N. Tas, J. Wissink, L. Sander, T. Lammerink and M. Elwenspoek, "The Shuffle Motor: A High Force, High Precision Linear Electrostatic Stepper Motor," *Proceedings of the 1997 International Conference on Solid–State Sensors and Actuators*, Jun. 16–19, 1997, pp. 777–780.

M.P. de Boer and T.A. Michalske, "Improved Autoadhesion Measurement Method for Micromachined Polysilicon Beams," *Material Research Society Symposium Proceedings*, vol. 444, 1997, pp. 87–92.

U. Srinivasan, J.D. Foster, U. Habib, R.T. Howe and R. Maboudian, "Lubrication of Polysilicon Micromechanisms with Self–Assembled Monolayers," *Proceedings of the Solid–State Sensor and Actuator Workshop*, Hilton Head Island, SC, Jun. 8–11, 1998, pp. 156–161.

M.P. de Boer, J.M. Redmond and T.A. Michalske, "A Hinged–Pad Test Structure for Sliding Friction Measurement in Micromachining," *Proceedings of the SPIE Conference on Materials and Device Characterization in Micromachining*, Santa Clara, CA, Sep. 1998, SPIE vol. 3512, pp. 241–250.

J.M. Redmond, M.P. de Boer and T.A. Michalske, "Integrated Modeling of a Micro Hinged Structure for Sliding Friction Measurement," Presented at the ASME International Mechanical Engineering Congress and Exposition, Anaheim, CA, Nov. 18, 1998.

* cited by examiner

Primary Examiner—Robert Raevis
(74) Attorney, Agent, or Firm—John P. Hohimer

(57) ABSTRACT

A microelectromechanical (MEM) friction test apparatus is disclosed for determining static or dynamic friction in MEM devices. The friction test apparatus, formed by surface micromachining, is based on a friction pad supported at one end of a cantilevered beam, with the friction pad overlying a contact pad formed on the substrate. A first electrostatic actuator can be used to bring a lower surface of the friction pad into contact with an upper surface of the contact pad with a controlled and adjustable force of contact. A second electrostatic actuator can then be used to bend the cantilevered beam, thereby shortening its length and generating a relative motion between the two contacting surfaces. The displacement of the cantilevered beam can be measured optically and used to determine the static or dynamic friction, including frictional losses and the coefficient of friction between the surfaces. The test apparatus can also be used to assess the reliability of rubbing surfaces in MEM devices by producing and measuring wear of those surfaces. Finally, the friction test apparatus, which is small in size, can be used as an in situ process quality tool for improving the fabrication of MEM devices.

51 Claims, 18 Drawing Sheets

Cross-Section 1 - 1

Cross-Section 2 - 2

Cross-Section 3 - 3

Cross-Section 4 - 4

Cross-Section 5 - 5

MICROMACHINE FRICTION TEST APPARATUS

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to micromachining, and in particular to a test apparatus for measuring friction or wear on a microscopic scale. The test apparatus can further be used as a microelectromechanical (MEM) fabrication process quality tool, and also as a test structure for assessing the reliability of MEM devices.

BACKGROUND OF THE INVENTION

In microelectromechanical (MEM) devices, surface forces can play a relatively large role compared to gravity and inertia, which are the dominating forces on a macroscopic scale. High static friction is known to contribute to wear in MEM devices and can lead to device seizure, whereas kinetic friction (also termed dynamic friction) consumes a significant portion of the motive torque between rubbing or sliding members in a MEM device. Investigations into the failure modes of electrostatic microengines, for example, indicate that the usual path to failure involves adhesion between rubbing surfaces. Since surface forces are not well characterized and are often difficult to reproduce in MEM devices, most commercial MEM devices avoid any contact between structural members. If, however, sliding contact between the structural members of a MEM device is allowed, many more types of MEM devices can be fabricated, including shuffle motors and self-assembling structures (e.g. pop-up mirrors).

Relatively little is understood about friction on a microscopic scale in a MEM device when two surfaces come into contact. Thus, it is not currently understood how friction scales with apparent pressure, or with sliding velocity. Here, apparent pressure is that pressure which would be calculated for two surfaces coming into contact with each other when the two surfaces are assumed to be perfectly smooth. In a MEM devise, the actual pressure between these two surfaces can be substantially different when the roughness of the surfaces is taken into account. Thus, 2–10 nanometers of root-mean-square (rms) surface roughness which can be achieved in a MEM device can result in an actual pressure that is about one to two orders of magnitude larger than the apparent pressure would be for perfectly smooth surfaces.

In MEM devices, the apparent pressure and sliding velocity can vary by orders of magnitude depending upon a particular type of MEM device or on a range of operation of the device, with the apparent pressure generally varying in the range of about 0.1–100 megaPascal (MPa), and with the sliding velocity generally varying in the range of about 0.1–1000 microns per second ($\mu$m-s$^{-1}$). Previous characterizations of friction on horizontal surfaces in MEM devices has been obtained using reciprocating comb-drive structures with contact between nonplanar surfaces. A disadvantage of these previous characterization methods is that the data could be obtained only over a limited range of pressure on the order of tens of kiloPascals due to a limited force which can be generated using a comb-drive structure. A further disadvantage of the previous method for measuring friction is that the comb-drive structure occupies a relatively large area on a semiconductor substrate, thereby limiting the area available for other MEM devices.

What is needed is a compact device for measuring friction on a microscopic scale over a relatively large range of pressure and velocity. Such a device could be incorporated onto a semiconductor substrate as a test structure to measure basic properties of friction that could then be used to model the behavior of other MEM devices fabricated on the same substrate.

An advantage of the present invention is that it provides a solution to a critical need to characterize the frictional properties of contacting surfaces for microelectromechanical devices and systems.

A further advantage of the present invention is that it provides an in situ test apparatus for determining friction and/or wear on contacting surfaces that have undergone a specified sequence of fabrication steps, thereby serving as a diagnostic process monitor.

Yet another advantage is that the friction test apparatus of the present invention occupies a relatively small substrate area compared to prior comb-drive structures, thereby allowing the apparatus of the present invention to be fabricated alongside a number of other MEM devices on a substrate for use in assessing the quality and reliability of the fabricated MEM devices.

Still a further advantage of the friction test apparatus of the present invention is that it allows friction measurements to be made over a much greater range of applied contacting pressure than is possible with prior devices, with the applied contacting pressure being independently controllable and variable from a horizontally-applied pressure used to generate a sliding motion of the apparatus.

These and other advantages of the present invention will become evident to those skilled in the art.

SUMMARY OF THE INVENTION

The present invention relates to a friction test apparatus that comprises a pair of substantially planar contacting surfaces including a first surface formed above a substrate and a second surface formed on an elongate friction pad suspended above the substrate over the first surface and moveable into contact with the first surface for static or dynamic friction measurements. A rubbing motion of the first and second surfaces can be produced with the apparatus laterally along a longitudinal axis of the first surface. The friction test apparatus further comprises means for providing an adjustable vertically-directed force (i.e. a contacting force) to bring the second surface into contact with the first surface, and means for providing an adjustable horizontally-directed force to effect lateral movement of the second surface relative to the first surface.

In a preferred embodiment of the present invention, the friction test apparatus comprises a cantilevered driver beam supported at one end thereof above the substrate and substantially co-planar with the substrate, with an elongate friction pad suspended from the other end of the cantilevered beam. The end of the cantilevered beam upon which the friction pad is suspended can be forked with the friction pad attached to the forked end of the beam by one or more hinges. A bottom surface of the friction pad forms the second surface. Each hinge can be offset a distance from the end of the friction pad nearest the driver beam to maximize an area of contact between the first and second surfaces over a predetermined range of applied pressure. The contact pad containing the first surface can be formed on the substrate below the friction pad. In some embodiments of the present invention, more than one friction pad can be suspended from the cantilevered driver beam.

The means for providing the vertically-directed force can be a first electrostatic actuator comprising a pair of electrodes on each side of the friction pad to bring the friction pad into mechanical contact with the contact pad. In response to a first applied voltage, $V_1$, a vertically-directed electrostatic force of attraction is generated between these electrodes to move the friction pad downward toward the substrate and into mechanical contact with the contact pad. The vertically-directed force is adjustable by controlling the magnitude of the first applied voltage, $V_1$ which can be provided by a power supply or signal generator, with or without computer control.

The means for providing the horizontally-directed force can be the driver beam which preferably includes thereon an upper central electrode that is superposed above a lower central electrode located above the substrate to form a second electrostatic actuator for moving the friction pad laterally along the contact pad. These central electrodes are responsive to a second applied voltage, $V_2$, to electrostatically bend the driver beam, shortening its horizontal extent, and thereby generating the horizontally-directed force to move the friction pad laterally along the contact pad. The horizontally-directed force can be adjusted by controlling the second applied voltage, $V_2$ which can be provided by a power supply or signal generator, with or without computer control. A cyclic second applied voltage, $V_2$, can be used to generate a rubbing motion between the first and second surfaces to determine dynamic friction between the surfaces, or to produce wear between the surfaces for assessing the reliability of contacting surfaces in other MEM devices formed on, the substrate.

The MEM friction test apparatus can further comprise means for determining a lateral displacement of the friction pad along the contact pad for use in calculating, in combination with the vertically- and horizontally-directed forces, a measure of friction between the friction pad and the contact pad. The means for determining the lateral displacement can comprise an optical interferometer, or a light beam (e.g. from a laser) that is directed onto an upper surface of the driver beam at an angle and reflected or bounced off the driver beam so that a spatial position of the reflected light beam can be sensed (e.g. by a position-sensing detector), or a pair of diffraction gratings, preferably with different grating periods, including a stationary grating on the substrate and a moveable grating on the driver beam above the stationary grating (i e. forming a Moiré interferometer).

The friction test apparatus can be used to measure friction between surfaces of different materials, with at least one of the friction pad and the contact pad generally comprising a material such as polycrystalline silicon (also termed polysilicon), silicon nitride, a dielectric (e.g. alumina), a metal (e.g. aluminum) or a metal alloy. The friction to be determined with the apparatus can be either static friction or dynamic friction (i.e. friction of motion), with the dynamic friction being measurable as a function of the velocity of movement of the friction pad laterally along the contact pad upon repeated actuation of the second electrostatic means with an alternating-current (ac) voltage, $V_2$. Additionally, the apparatus can be used to measure a frictional loss resulting from a rubbing of the friction pad against the contact pad, or a force or energy of adhesion (also termed stiction) between the friction pad and the contact pad. Furthermore, the apparatus has applications for measuring wear within a MEM device, for assessing the reliability of one or more MEM devices fabricated on the same substrate as the friction test apparatus, or for use as a process quality tool during the fabrication of MEM devices.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1A:
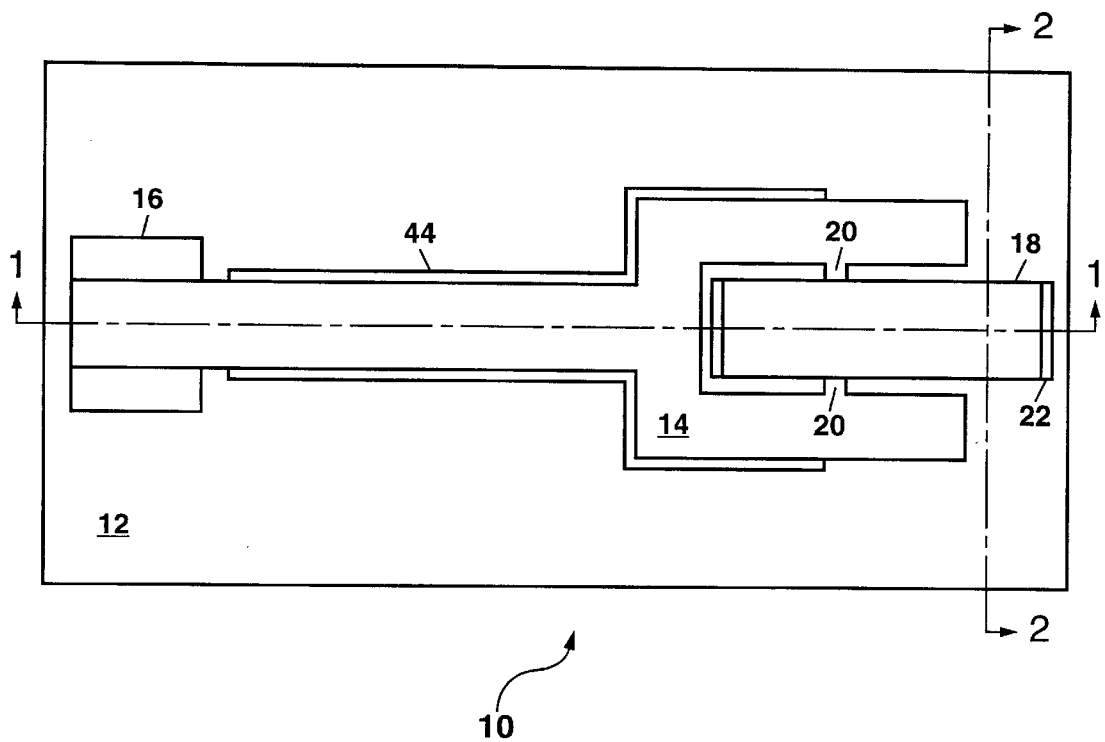
FIG. 1a shows a schematic plan view of a first embodiment of the MEM friction test apparatus of the present invention.
Figure 1B:
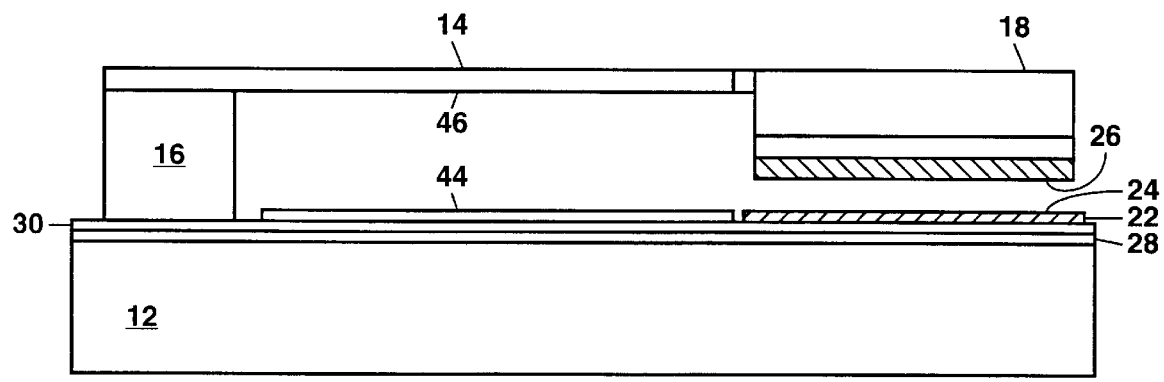
FIG. 1b shows a schematic cross-section view of the first embodiment of the MEM friction test apparatus along the line 1—1.
Figure 1C:
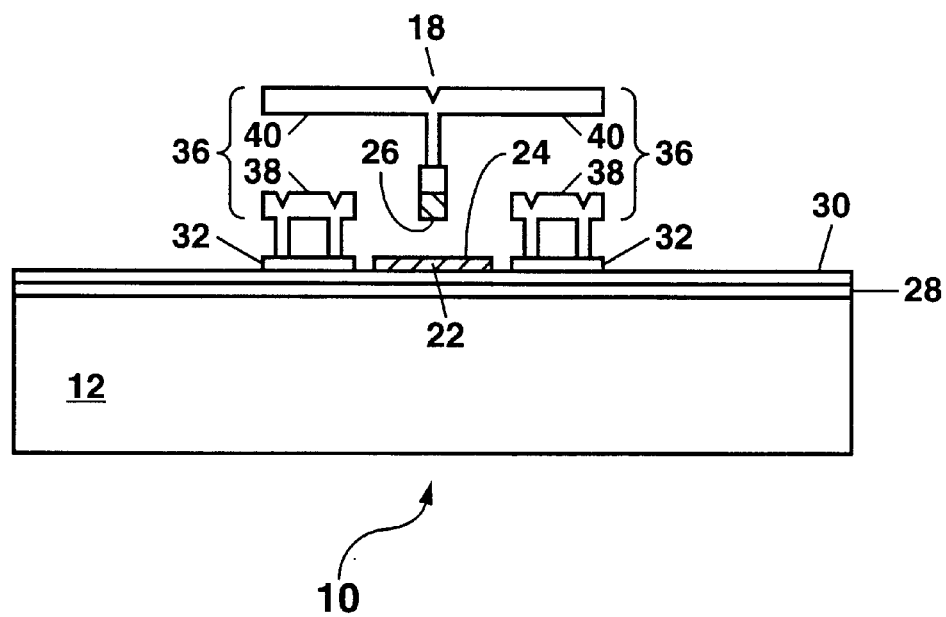
FIG. 1c shows a slightly enlarged schematic cross-section view of the first embodiment of the MEM friction test apparatus along the line 2—2.

The present invention relates to a microelectromechanical (MEM) friction test apparatus 10 which according to a first embodiment thereof is shown schematically in FIGS. 1a–1c. FIG. 1a shows a schematic plan view of the friction test apparatus 10 which is formed on a substrate 12 and comprises a cantilevered driver beam 14 that is supported at one end above the substrate 12 by a support post 16 so that the driver beam 14 in the absence of any applied voltages is substantially co-planar with the substrate 12. The other end of the driver beam 14 can be forked as shown in FIG. 1a. The friction test apparatus 10 further comprises an elongate friction pad 18 which can be connected to the forked end of the driver beam 14 by a pair of hinges 20 attached to opposite sides of the friction pad 18. Underlying the friction pad 18 is a contact pad 22 that is formed on the substrate 12.

The friction test apparatus 10 can be used to bring two surfaces into contact to study and quantify friction on a microscopic scale to solve problems that can occur with MEM devices and to develop improved MEM devices. It should be noted that the friction test apparatus 10 is itself a MEM device and is fabricated using the same processes and materials that are generally used for the manufacture of MEM devices. Thus, by fabricating the friction test apparatus 10 on a substrate 12 alongside one or more other types of MEM devices, the friction test apparatus 10 can provide valuable information about the behavior and reliability of the other types of MEM devices.

In the embodiment of the present invention in FIGS. 1a–1c, the two contacting surfaces include a first surface 24 that comprises a top surface of the contact pad 22, and a second surface 26 that comprises a bottom surface of the friction pad 18. The first and second surfaces, 24 and 26, can be comprised of the same or different materials (e.g. polysilicon, silicon nitride, a dielectric, a metal or a metal alloy) that are deposited as layers over the substrate 12, with at least one of the first and second surfaces, 24 and 26, generally comprising polysilicon. In FIGS. 1a–1c, the layers containing the first and second surfaces, 24 and 26, are shown cross-hatched for clarification. Additional layers of deposited and patterned material can be used to form one or both of the friction pad 18 and the contact pad 22.

In the first embodiment of the present invention in FIGS. 1a–1c, the friction test apparatus 10 further comprises a first electrostatic means for providing a vertically-directed force to bring the friction pad 18 into mechanical contact with the contact pad 22, and a second electrostatic means for providing a horizontally-directed force to move the friction pad 18 laterally along the contact pad 22 by a predetermined distance. Thus, the present invention provides a way of bring the first and second surfaces, 24 and 26, into mechanical contact with each other with an adjustable force of contact, and also a way of effecting a lateral movement of the second surface 26 relative to the first surface 24. In this way both static and dynamic friction can be characterized on a microscopic scale. Additionally, the friction test apparatus 10 of the present invention is also useful for characterizing stiction. Finally, the apparatus 10 can be used to characterize wear between the first and second surfaces rubbing together when the horizontally-directed force is cyclic.

The friction test apparatus 10 in FIGS. 1a–1c can be formed by conventional surface micromachining processes as known to the art. The process for forming the friction test apparatus 10 will be described hereinafter with reference to FIGS. 2a–2o which are based on the schematic cross-sectional view of FIG. 1c.

A large number of individual process steps can be used to form the friction test apparatus 10 and any other MEM devices to be fabricated on the substrate 12 using the same process steps. Therefore, only the handful of process steps that are relevant to the present invention will be described in detail. Those skilled in the art will understand the use of other conventional integrated circuit (IC) or micromachining process steps which will not be described in detail herein. Such conventional process steps include, for example, various material deposition processes, the formation of a mask (e.g. a photoresist mask, or a hard mask comprising about 500 nanometers of patterned TEOS patterned by etching using an overlying photoresist mask which is then removed) overlying a material layer in preparation for defining features into the layer by etching. Such conventional process steps further include etching (e.g. reactive ion etching) for removing material from the masked layer at locations corresponding to openings in the mask; stripping of the mask after the etching is complete; and various cleaning processes. Additionally, those skilled in the art will understand that the term "patterning" as used herein refers to a sequence of well-known processing steps including applying a photoresist to the substrate 12, prebaking the photoresist, aligning the substrate 12 with a photomask, exposing the photoresist through the photomask, developing the photoresist, baking the wafer, etching away the surfaces not protected by the photoresist, and stripping the protected areas of the photoresist so that further processing can take place.

The substrate 12 generally comprises a monocrystalline silicon wafer or a portion thereof. Upon the substrate 12 are deposited and patterned a series of material layers, including layers of polysilicon and a sacrificial material (e.g. silicon dioxide or a silicate glass). These layers can be deposited by conventional deposition processes, including chemical vapor deposition (CVD), low-pressure CVD (LPCVD), and plasma-enhanced CVD (PECVD).

Figure 2A:
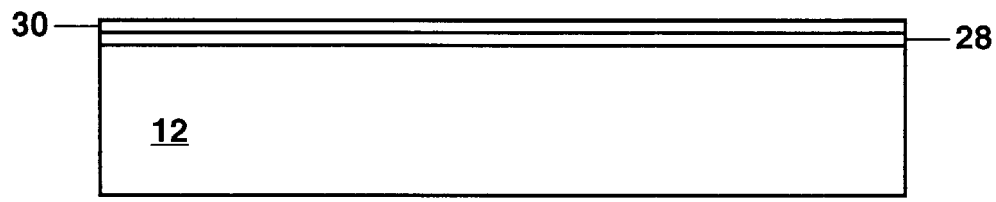
FIGS. 2a–2o illustrate in schematic cross-section view a series of process steps for forming the first embodiment of the friction test apparatus as shown in FIG. 1c.

In FIG. 2a, a silicon substrate 12 can be initially prepared for use in fabricating the friction test apparatus 10 by blanketing the substrate 12 with a layer of thermal oxide 28 (e.g. 0.6 μm thick) formed by a conventional silicon oxidation process at an elevated temperature (e.g 1050° C. for about 1.5 hours). A layer of low-stress silicon nitride 30 (e.g. 0.8 μm thick) can then deposited over the thermal oxide layer using LPCVD at about 850° C. The thermal oxide and silicon nitride layers provide electrical isolation from the substrate for overlying elements of the friction test apparatus 10.

Figure 2B:
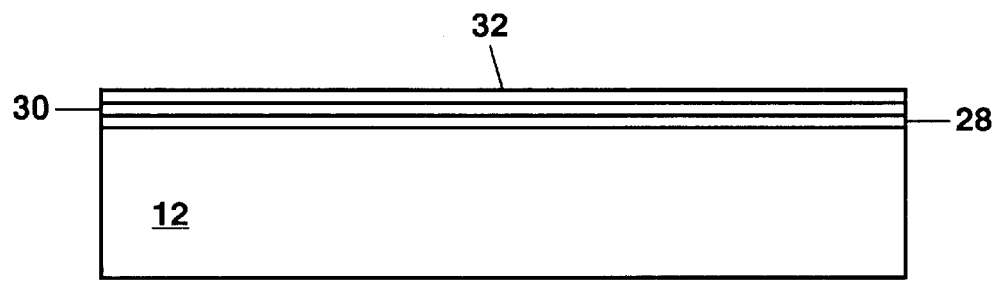

In FIG. 2b, a first polysilicon layer 32 (termed herein as a Poly-0 layer) is deposited over the substrate 12, blanketing the silicon nitride layer. All polysilicon depositions described herein are performed by LPCVD at a temperature of about 580° C. Phosphorous n-type doping can be used to make the first polysilicon layer and other of the polysilicon layers described hereinafter electrically conductive as needed (e.g. for forming the electrical connections to the apparatus 10 and for forming the electrostatic actuators).

Figure 2C:
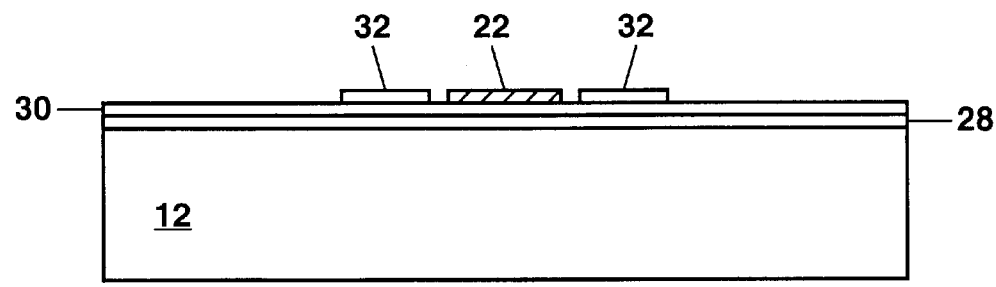

In FIG. 2c, after deposition, the first polysilicon layer 32 can be patterned for use in forming various elements of the friction test apparatus 10 and other MEM devices (not shown) that can also be formed on the substrate 12 adjacent to the apparatus 10. The first polysilicon layer 32 as shown in FIG. 2c forms a part of each electrostatic actuator that is used to operate the friction test apparatus 10, forms a polysilicon contact pad 22, and forms electrical connections from bond pads or probe pads to the electrostatic actuators (not shown).

Figure 2D:
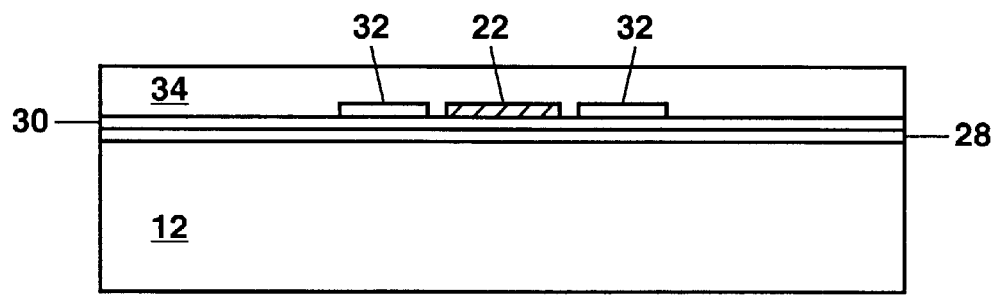

In FIG. 2d, a first layer of a sacrificial material 34 is blanket deposited over the substrate 12 and planarized by chemical-mechanical polishing (CMP). A total thickness of the first layer of the sacrificial material 34 can be, for example, 2.1 μm after the CMP step. The CMP step can be used to precisely adjust the thickness of the first layer of the sacrificial material 34 and any subsequent layers thereof. In general, the thickness of the first layer of the sacrificial material 34 in FIG. 2d is selected so that the first and second surfaces, 24 and 26 will come into contact while a first electrostatic actuator 36 comprising one or more stationary electrodes 38 attached to the substrate 12 and one or more moveable electrodes 40 attached to the friction pad 18 and superposed over the stationary electrodes 38 will not be electrically shorted out by physical (i.e. mechanical) contact of the electrodes 38 and 40.

The sacrificial material 34 comprises a material that can be selectively etched away later with an etchant that does not substantially attack polysilicon. Particular types of sacrificial materials 34 that can be used for practice of the present invention include silicon dioxide and silicate glasses. A preferred silicate glass, termed TEOS, can be deposited from the decomposition of tetraethylortho silicate by LPCVD at about 750° C., and densified by subsequent high temperature processing.

Figure 2E:
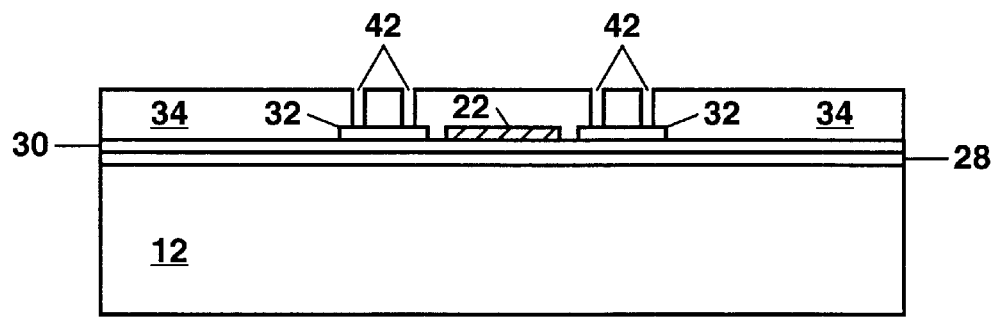

In FIG. 2e, a plurality of trenches 42 are etched down through the first layer of the sacrificial material 34 to the underlying Poly-0 layer 32. The trenches 42 can be photo-lithographically defined and dry etched (e.g. by reactive ion etching). Additional trenches and shaped openings (not shown) can be formed through the first layer of the sacrificial material 34 at the locations of the support post 16 and a lower central electrode 44 (see FIG. 1b). The lower central electrode 44 together with a superposed upper central electrode 46 forms a second electrostatic actuator which can be used to electrostatically force the driver beam 14 downward toward the substrate in response to a second applied voltage, $V_2$. This shortens the length of the driver beam 14, thereby generating the horizontally-directed force to move the friction pad 24 laterally across the contact pad 22.

Figure 2F:
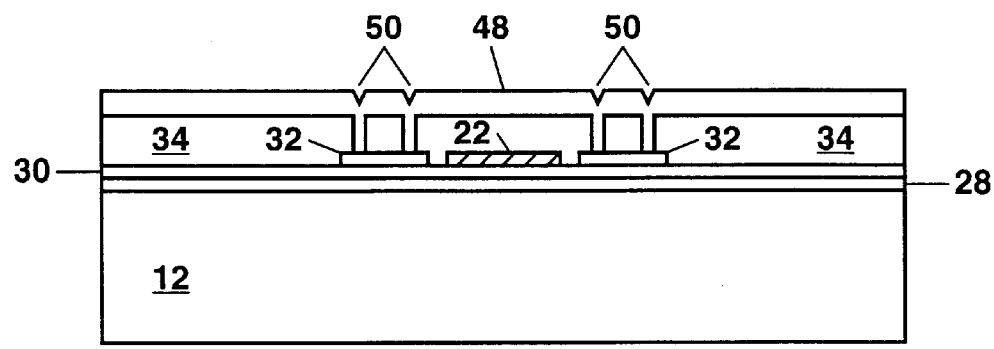

In FIG. 2f, a second layer of doped polysilicon 48 (denoted herein as the Poly-1 layer) is blanket deposited over the substrate 12 to a depth of, for example, 1 μm. The Poly-1 layer 48 also fills in the trenches 42 and the other openings in the first layer of the sacrificial material 34. The Poly-1 layer 48 will be used to form the stationary electrodes 38 and the lower central electrode 44. The Poly-1 layer 48 can also form a part of the friction pad 18 and define the second surface 26. Finally, a portion of the Poly-1 layer 48 deposited in the trenches can be used to electrically connect the stationary electrodes 38 and the lower central electrode 44 to the underlying Poly-0 layer 32 wherein electrical connections from bonding or probe pads (not shown) to the electrodes 38 and 44 can be made. The Poly-1 48 layer can be optionally planarized by CMP to remove any dimples 50 formed in the Poly-1 layer 48 over the trenches 42 as shown in FIG. 2f.

Figure 2G:
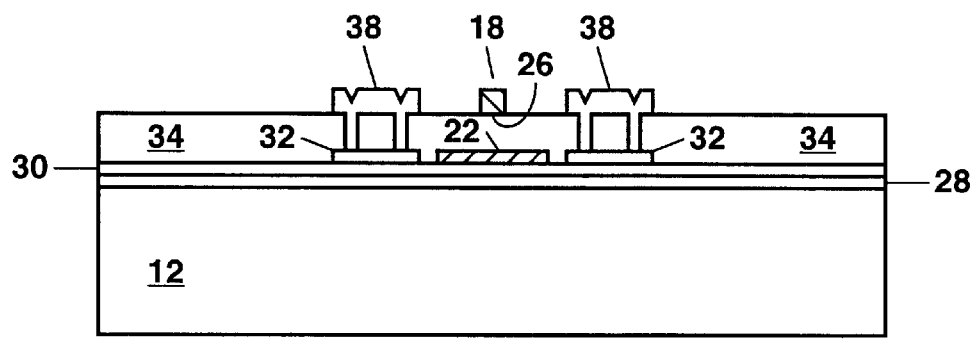

In FIG. 2g, the Poly-1 layer 48 is patterned by etching (e.g. reactive ion etching) to form the stationary electrodes 38 and the lower central electrode 44 (not shown). Additionally, the Poly-1 layer 48 can be used to build up the support post 16 and to begin to build up the elongate friction pad 18 with the second surface 26.

Figure 2H:
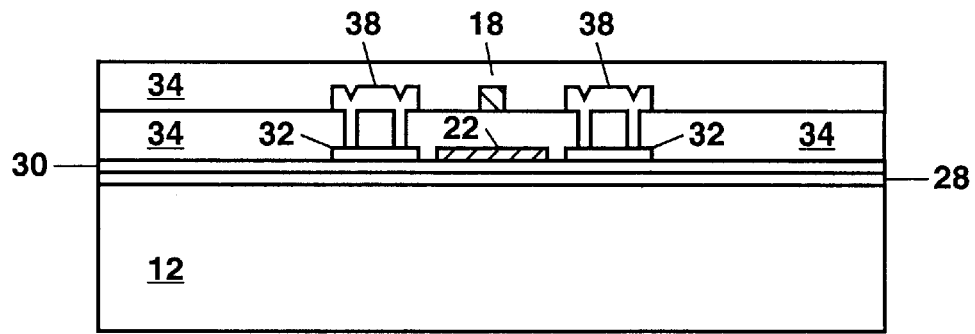
Figure 2I:
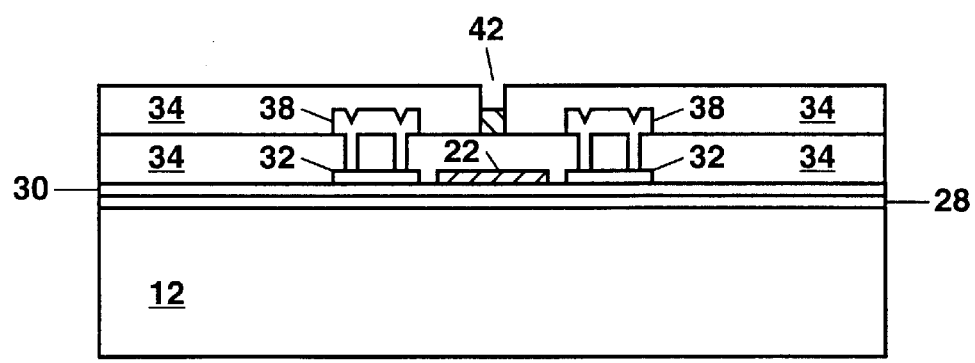

In FIG. 2h, a second layer of the sacrificial material 34 is deposited to blanket the substrate 12, and is planarized by CMR The second layer of the sacrificial material 34 can be about 2 μm thick with a composition as described previously. In FIG. 2i, another trench 42 can be etched through the second layer of the sacrificial material 34 to expose the portion of the friction pad 18 previously formed in FIG. 2g.

Figure 2J:
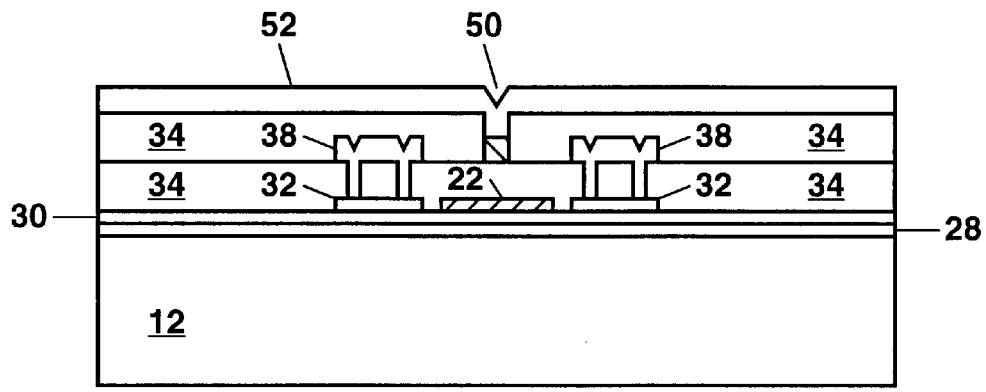
Figure 2K:
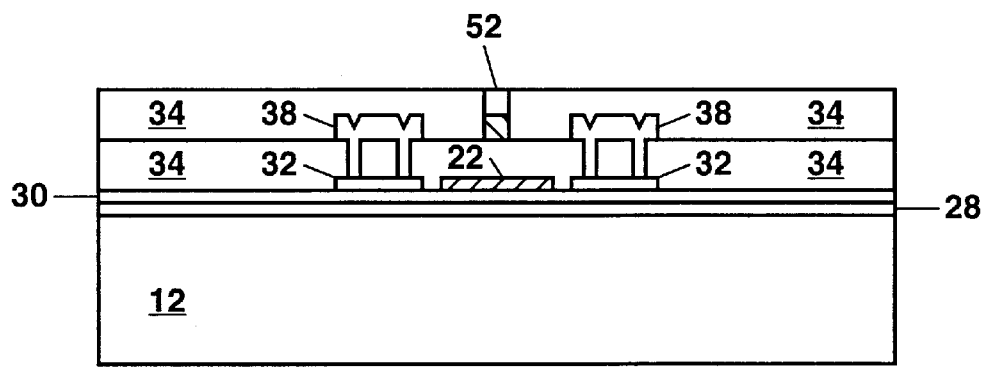

In FIG. 2j, a third layer of polysilicon 52 (denoted herein as the Poly-2 layer) is blanket deposited over the substrate 12 to a depth of, for example, 1–2 μm and fills in the trench 42 and the other openings in the second layer of the sacrificial material 34 to further build up the support post 16 and the friction pad 18. In FIG. 2k, any of the Poly-2 layer 52 remaining above the trench 42 after this deposition step can be removed by etching, or by CMP.

Figure 2L:
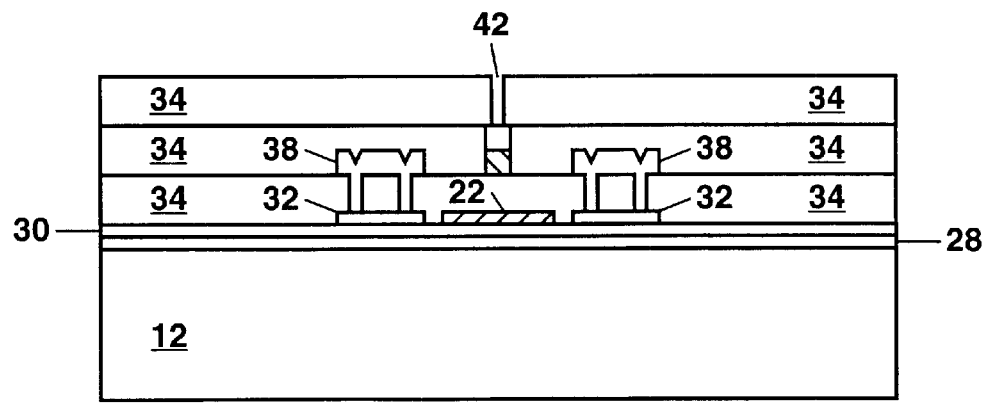

In FIG. 2l, a third layer of the sacrificial material 34 is blanket deposited over the substrate 12 and patterned by etching to form another trench 42 at the location of the friction pad 18, and a shaped opening (not shown) at the location of the support post 16. If necessary, a CMP step can be used to planarize the third layer of the sacrificial material 34, or to precisely adjust its thickness which can be, for example, about 2 μm.

Figure 2M:
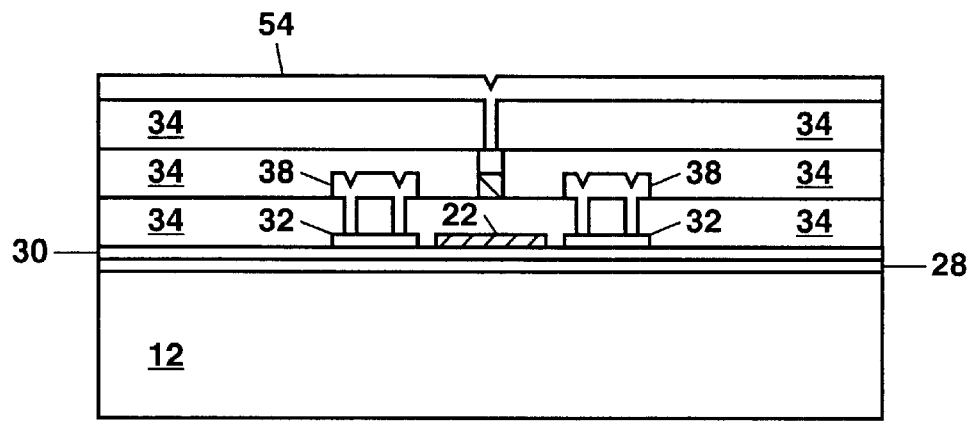

In FIG. 2m, a fourth layer of polysilicon 54 (denoted herein as the Poly-3 layer) is blanket deposited over the substrate 12 to a depth of, for example, 1–2 μm to fill in the trench 42 and the shaped opening in the third layer of the sacrificial material 34, thereby further building up the friction pad 18 and the support post 16, respectively.

Figure 2N:
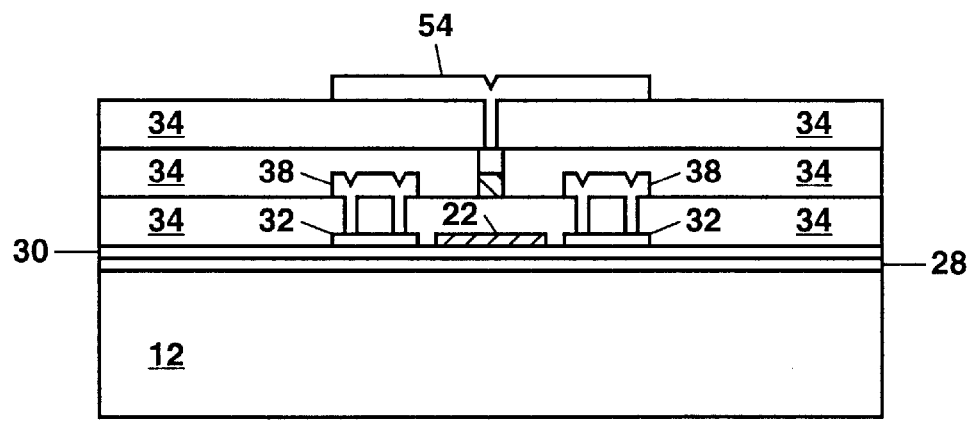

In FIG. 2n, the Poly-3 layer 54 can be patterned by etching (e.g. reactive ion etching) to form the remainder of the friction pad 18. Additionally, the Poly-3 layer 54 can be used to form the cantilevered driver beam 14 an d the hinges 20 (see FIGS. 1a and 1b). The entire Poly-3 layer 54 can be made electrically conductive by n-type doping with phosphorous (e.g. by ion implantation), thereby forming the upper central electrode 46 on the driver beam 14, and also forming the moveable electrodes 40 on the friction pad 18. For operation of the friction test apparatus 10, the upper central electrode 46 and the moveable electrodes 40 are preferably electrically connected together and maintained at ground potential.

Figure 2O:
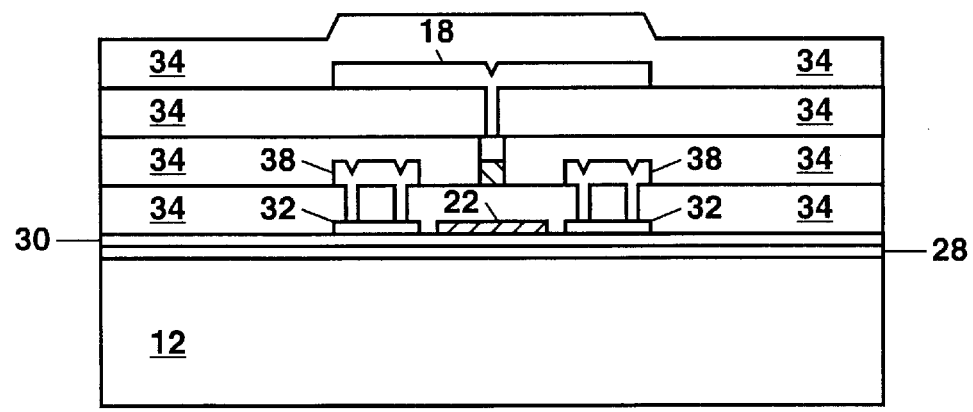

In FIG. 2o, a final layer of the sacrificial material 34 can be blanket deposited over the substrate to encapsulate the friction pad 18 and the various other elements of the friction test apparatus 10 in preparation for a thermal annealing step. The thermal annealing step, which is used to relieve any stress in the polysilicon layers and to minimize any stress-induced bending of the driver beam 14, can be performed, for example, by heating the substrate 12 to an elevated temperature of 1100° C. for three hours.

To release the friction test apparatus 10 for operation as shown in FIGS. 1a–1c, an etch release step can be performed to selectively etch away the sacrificial material 34. The etch release step can be performed using a selective etchant comprising hydrofluoric acid (HF) as a vapor or liquid to dissolve away the sacrificial material 34 entirely or in part while not substantially attacking polysilicon or other materials (e.g. silicon nitride, alumina, metals or metal alloys) used in forming the completed friction test apparatus 10. An example of such a release etchant is a 1:1 solution of hydrochloric acid (HCl) and HF. Alternately, a buffered HF solution or HF vapor can be used. To aid in the etch release process, the friction pad 18 and other elements of the friction test apparatus 10 formed of polysilicon can include a plurality of generally micron-sized access holes (not shown) etched through the polysilicon elements at spaced intervals.

After the etch removal step, the substrate 12 can be washed in a hydrogen peroxide ($H_2O_2$)/water solution and dried with supercritical carbon dioxide ($CO_2$). After the $H_2O_2$ wash, surfaces within the friction test apparatus 10 are nominally hydrophilic, and a 1-nm-thick oxide covers the surfaces to aid in preventing stiction. Alternately, a self-assembling monolayer can be deposited to coat the surfaces to prevent stiction and to reduce friction.

Typical dimensions for the various elements of the first embodiment of the friction test apparatus 10 in FIGS. 1a–1c are as follows. The driver beam 14 can be about 500 $\mu$m long and 50 $\mu$m wide. The friction pad 18 can be about 200–600 $\mu$m long and about 60 $\mu$m wide at the top, with the second surface 26 being typically 3 $\mu$m wide. The hinges 20 can be about 2–10 $\mu$m wide (in a direction parallel to the length of the friction pad 18) and 5 $\mu$m wide. The dimensions of the hinges 20 can be selected to provide a predetermined level of stiffness or compliance. A stiff hinge 20 reduces the compliance; whereas a more flexible hinge 20 reduces a moment produced by the driver beam 14, thereby increasing the flatness of the friction pad 18 at a lower voltage, $V_1$. The stationary electrodes 38 can have a length equal to that of the friction pad 18 and a width of typically 25 $\mu$m. In an as-fabricated or rest position, the gap between the stationary electrodes 38 and the moveable electrodes 40 can be 3 $\mu$m; and the gap between the central electrodes, 44 and 46, can be 6 $\mu$m.

Figure 3A:
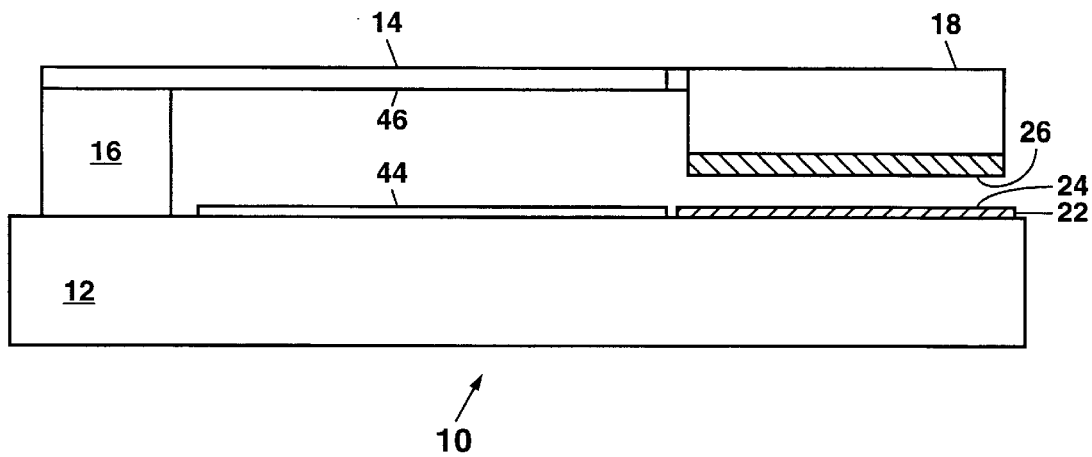
FIGS. 3a–3c illustrate operation of the first embodiment of the friction test apparatus.
Figure 3B:
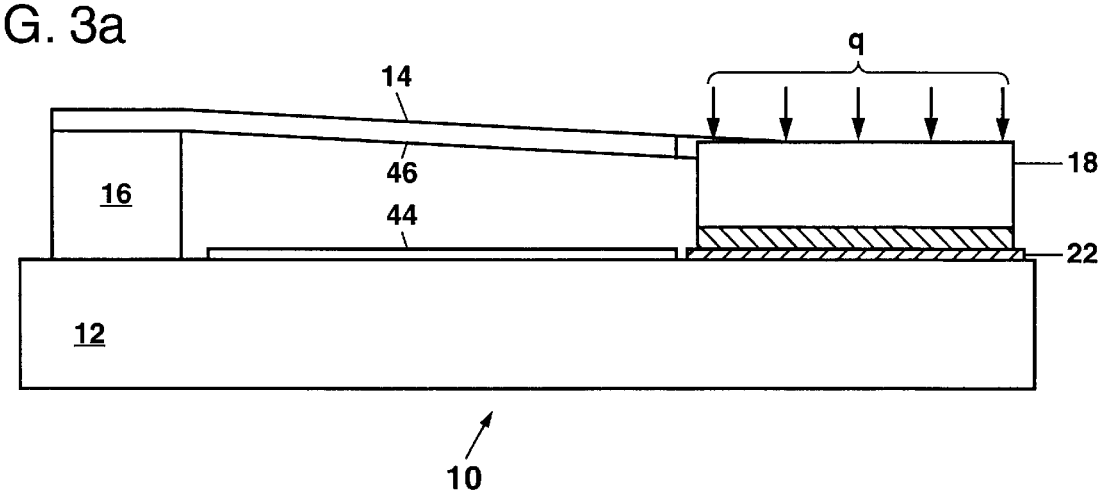
Figure 3C:
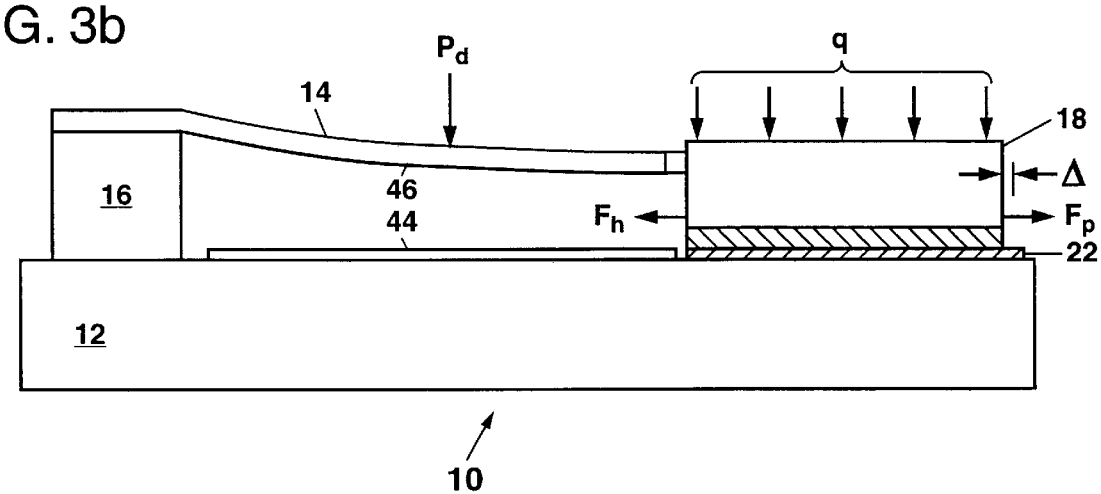

Operation of the friction test apparatus 10 of the present invention can be understood with reference to a simplified cross-sectional view of the first embodiment of the friction test apparatus 10 as shown in FIGS. 3a–3c.

FIG. 3a shows the friction test apparatus 10 in an as-fabricated state with the cantilevered driver beam 14 being substantially parallel to the substrate 12 and supporting the friction pad 18 above the contact pad 22 so that the first and second surfaces, 24 and 26, are spaced apart by about 2 $\mu$m.

In FIG. 3b, a first voltage, $V_1$, is applied between the stationary electrodes 38 and the moveable electrodes 40 of the first electrostatic actuator 36, with the moveable electrodes 40 preferably being held at ground potential (see also FIG. 1c). This first applied voltage, $V_1$, which is a direct-current (dc) voltage, generates a vertically-directed electrostatic force, q, between the stationary and moveable electrodes, 38 and 40, which is applied to the friction pad 18 to force the friction pad 18 downward into contact with the contact pad 22, thereby bringing the first and second surfaces, 24 and 26, together. Although the stationary electrodes 38 can be formed from the Poly-0 layer 32, the formation of these electrodes 38 in the Poly-1 layer 48 is advantageous since this brings the stationary electrodes 38 closer to the moveable electrodes 40 thereby increasing the vertically-directed force, q, which can be electrostatically generated for a given value of the first applied voltage, $V_1$.

Because of a restoring force generated by bending of the cantilevered driver beam 14 which is connected to the friction pad 18 through the hinges 20, the vertically-directed force, q, applied to the friction pad 18 cannot immediately produce a uniform contact between the first and second surfaces, 24 and 26, since these two surfaces are not perfectly parallel to each other when they first come into contact. However, beam theory can be used to determine an optimum placement for the hinges 20 that will maximize contact between the first and second surfaces, 24 and 26, at a relatively low value of the first applied voltage, $V_1$. Additionally, the optimum placement of the hinges 20 can help to resist any rocking of the friction pad 18 upon application of a second applied voltage, $V_2$, between the central electrodes, 44 and 46, to generate a downward force or loading, $P_d$, on the driver beam 14 which in turn will produce a horizontally-directed force, $F_h$ (see FIG. 3c). When the horizontally-directed force, $F_h$, exceeds a frictional force, $F_p$, due to contact between the first and second surfaces, 24 and 26, the second surface 26 will begin to slip across the first surface 24. Thus, the contact area between the first and second surfaces, 24 and 26, can be made nearly independent of the magnitude of the loading of the driver beam 14.

In FIG. 3b, when the first applied voltage, $V_1$, is increased to a few volts, the friction pad 18 is initially brought into contact with the contact pad 22. A further increase in the first applied voltage, $V_1$, can then be used to provide a controllable vertically-directed force, q, between the contacting first and second surfaces, 24 and 26. The thickness of the friction pad 18 formed from the Poly-1, Poly-2 and Poly-3 layers produces a highly uniform force or pressure per unit area across the width of the friction pad 18, since any flexure along this width of 3 $\mu$m is extremely small. The force of contact between the first and second surfaces, 24 and 26, can be adjusted by varying the magnitude of the first applied voltage, $V_1$, with the force of contact being adjustable over several orders of magnitude.

In FIG. 3c, once the friction pad 18 has been brought into contact with the contact pad 22 with a predetermined area of contact between the first and second surfaces, 24 and 26, a second voltage, $V_2$, can be applied between the central electrodes, 44 and 46, of the second electrostatic actuator. The effect of the second applied voltage, $V_2$, is to move the driver beam 14 closer to the substrate 12, thereby bending the driver beam 14 and shortening an effective length of the driver beam 14. As the effective length of the driver beam 14 is shortened, the friction pad 18 is forced to slide across the contact pad 22 towards the support post 16 over a slip distance, $\Delta$. The slip distance, $\Delta$, produced by a vertical deflection, w, at the midpoint of an inextensible driver beam 14 which cannot move vertically at either end thereof is:

$$\Delta = c\frac{w^2}{L_d}$$

where c is a constant given by c≈2 to first order, and $L_d$ is the length of the driver beam 14 in an as-fabricated or rest position. Thus, for a vertical deflection, w, of 2 $\mu$m and a driver beam length of $L_d$=500 $\mu$m, the slip distance, $\Delta$, is about 15–50 nanometers depending upon a particular embodiment of the present invention. While this slip distance is small, it can be sufficient to disengage contacting asperities on the first and second surfaces, 24 and 26, and to engage asperities at new points of contact since the aspherities have an average contact radius of 10 nanometers for the rms surface roughness of the deposited polysilicon layers used to form the first embodiment of the friction test apparatus 10.

In FIG. 3c, to first order about one-half the work done by the downward force, $P_d$, in deflecting the driver beam 14 by a distance, w, will induce slip in the contact pad 18 over a distance, $\Delta$. Thus, the horizontally-directed force, $F_h$, can be determined from the approximation:

$$F_h \approx \frac{P_d}{2} \cdot \frac{w}{\Delta}$$

Since the slip distance, $\Delta$, is much smaller than the deflection, w, the driver beam 14 acts as a force amplifier to generate a horizontally-directed force, $F_h$, which is much larger than the electrostatically-generated downward force, $P_d$. Thus, for a given coefficient of friction, $\mu$, slip between the first and second surfaces, 24 and 26, can be induced by the available force, $F_h$, over a wide range of applied pressure (i.e. the vertically-directed force, q) to the friction pad 18. This allows the coefficient of friction, $\mu$, to be measured over a wide range of applied pressure.

Figure 4A:
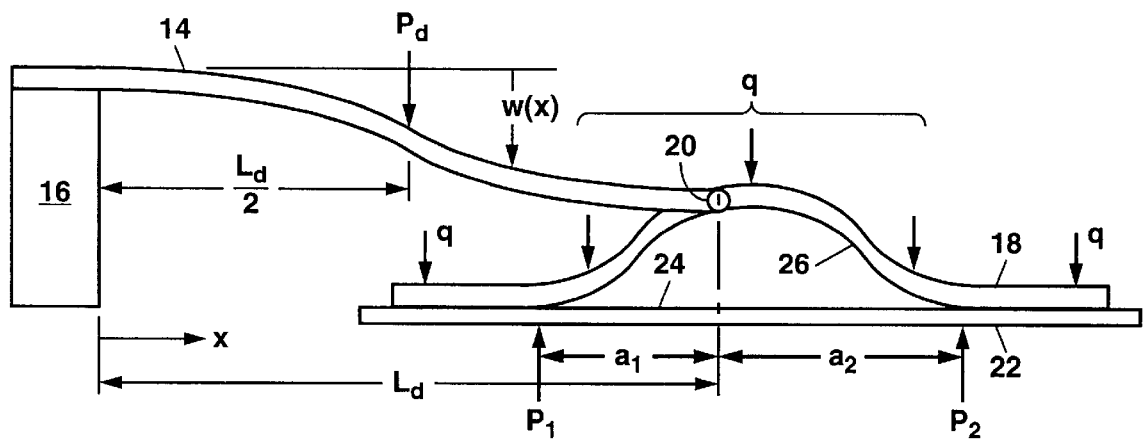
FIG. 4a shows a simplified beam model for determining the various deflections in the first embodiment of the friction test apparatus.

FIG. 4a shows a simplified beam model that can be used to simulate the various deflections in the first embodiment of the friction test apparatus 10 of FIGS. 1a–1c. This model is simplified to show only the contacting first and second surfaces, 24 and 26, respectively and the cantilevered driver beam 14 which is effectively coupled to the second surface 26 by hinge 20. The model is further based on a distributed loading of the friction pad 18 by the vertically-directed force, q, and a point loading of the downward force, $P_d$, at the center of the driver beam 14. Although in actuality the downward force, $P_d$, is distributed across the driver beam 14, the use of a point loading simplifies analytical modeling and allows deformation trends to be predicted. Less intuitive numerical calculations can be made using a distributed loading for the downward force, $P_d$, for comparison with the simplified model.

In an as-fabricated or rest position with no applied voltages, $V_1$ or $V_2$, the friction pad 18 is suspended above the first surface 24 of the contact pad 22. As the first voltage, $V_1$, is applied to the first electrostatic actuator and is increased, the vertically-directed force, q, increases to move the second surface 26 of the friction pad 18 downward into contact with the first surface 24 as shown in FIG. 4a. On a microscopic scale, the first and second surfaces, 24 and 26, generally do not come into complete contact with each other due to the connection of the friction pad 18 to the driver beam 14 by hinge 20. Thus, there are non-contacting distances, $a_1$ and $a_2$, along the length of the second surface 26 of the friction pad 18 on either side of the hinge 20 as shown in FIG. 4a.

In the simplified model of FIG. 4a, the reaction across the length of the friction pad 18 is comprised of uniform contact pressure between the first and second surfaces, 24 and 26, over the length of the longitudinal distance $x<L_d-a_1$ and also over the length $x>L_d+a_2$, where $a_1$ and $a_2$ are dependent on the magnitude of the vertically-directed force, q. Furthermore, in this simplified model, there are upwardly-directed point reactions, $P_1$ and $P_2$, which act at $x=L_d-a_1$ and $x=L_d+a_2$, respectively.

Figure 4B:
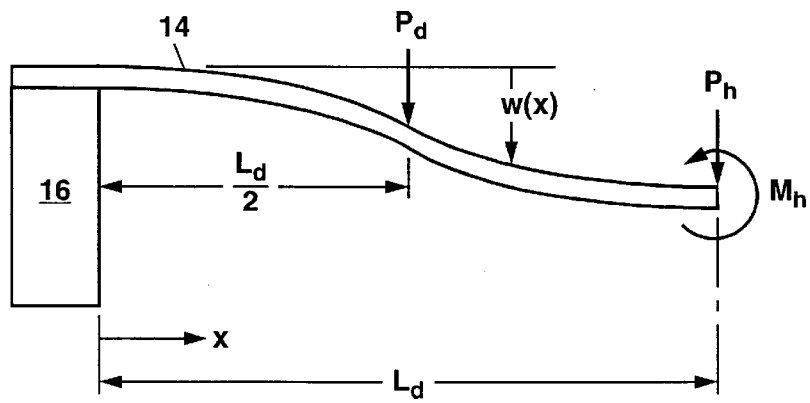
FIG. 4b shows a simplified beam model for determining a deflection of the cantilevered driver beam in the first embodiment of the friction test apparatus.

FIG. 4b shows a further simplification of the beam model of FIG. 4a that can be used to calculate a deflection, w(x), along the length of the driver beam 14. In FIG. 4b, the various forces and point reactions occurring over the length of the contact pad 18 in FIG. 4a are represented by an effective load, $P_h$, at the location of the hinge 20 and by an effective moment, $M_h$, acting about the hinge 20 as shown in FIG. 4b. The exact size of the effective load, $P_h$, and the size and direction of the effective moment, $M_h$, will depend upon the vertically-directed force, q, and the location of the hinge 20 along the length of the friction pad 18.

To solve for the deflection, w(x), for the friction pad 18 and the driver beam 14, force equations can be written for a left side and a right side of each of the friction pad 18 and the driver beam 14. The left and right sides of the friction pad 18 are defined by the location of the hinge 20; whereas the left and right sides of the driver beam 14 are defined by a midpoint of the driver beam 14 at $x=L_d/2$. At a given loading determined by the values of $P_d$ and q, boundary conditions can be applied to the force equations which can then be solved iteratively. Inextensibility of the driver beam 14 is assumed for these calculations.

Figure 5A:
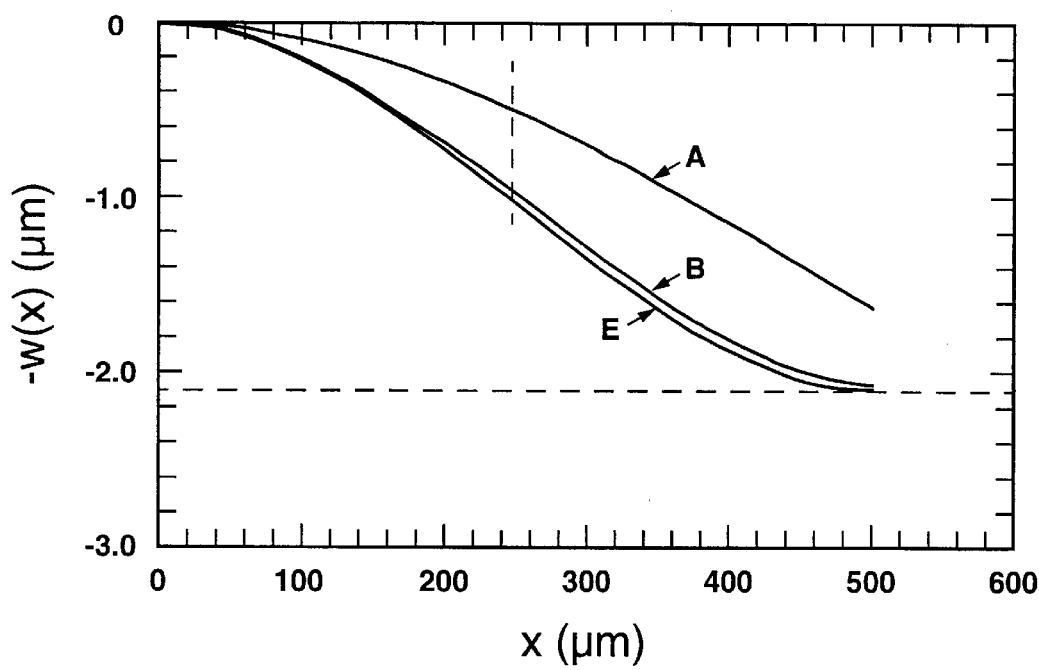
FIGS. 5a and 5b show simulations for the first embodiment of the friction test apparatus using the simplified beam model of FIGS. 4a and 4b with a variable electrostatic force applied to the friction pad, and with no electrostatic force applied to the driver beam.

FIG. 5a shows the results of simulations for a 500-$\mu$m-long driver beam 14 connected at the midpoint of a 200-$\mu$m-long friction pad 18 for various values of the first applied voltage, $V_1$, in the range of 2–30 volts, with the second applied voltage, $V_2=0$. In FIG. 5a, the vertical dashed line indicates the midpoint of the driver beam 14; and the horizontal dashed line indicates the location of the first surface 24 of the contact pad 22. Since the deflection, w(x), is measured from the as-fabricated or rest position of the driver beam 14, the negative of the deflection, $-w(x)$, is plotted in FIGS. 5a and 5b so that the calculated curves correspond to the shape of the driver beam 14 in the simplified beam models of FIGS. 4a and 4b.

The curve labelled "A" in FIG. 5a shows the deflection, $-w(x)$, of the driver beam 14 at $V_1=2$ volts corresponding to a value of q=20 Newtons per square meter (N-m$^{-2}$). At this value of the first applied voltage, $V_1$, the second surface 26 of the friction pad 18 just touches the first surface 24 of the contact pad 22 at its right extreme (see curve "F" in FIG. 5b which shows the deflection of the friction pad 18).

A further increase in $V_1$ to 8 volts produces a vertically-directed force of q=350 N-m$^{-2}$ which produces the shape in the driver beam 14 given by the curve labelled "B" in FIG. 5a. This increased force, q, further urges the second surface 26 into contact with the first surface 24 so that the slope at the right extreme of the second surface 26 becomes zero (see curve "G" in FIG. 5b which shows the deflection of the friction pad 18). However, at this voltage, $V_1$, the vertically-directed force, q, is not yet sufficient to bring a left-hand side of the second surface 26 into contact with the first surface 24. The large increase in the vertically-directed force, q, from 20 to 350 N-m$^{-2}$ that is needed to provide a zero slope for the limited area of contact of the first and second surfaces, 24 and 26, is due to a large bending resistance in the friction pad 18 along its longitudinal axis.

Figure 5B:
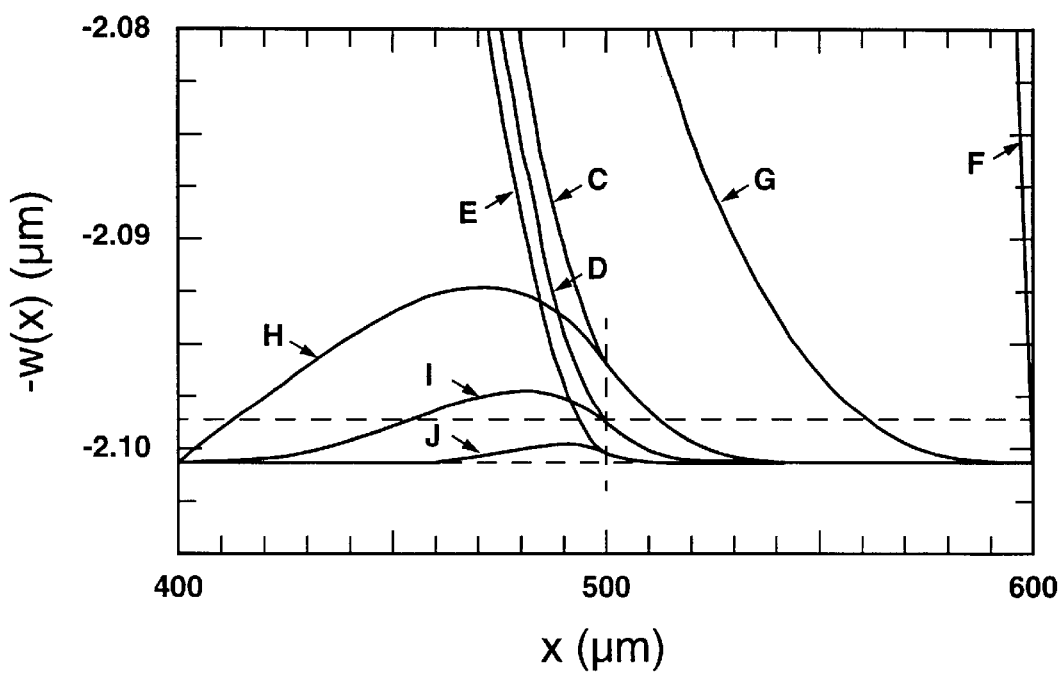

Increasing $V_1$ further to 10 volts increases the value of q to 600 N-m$^{-2}$ which is now sufficient to bring the left-hand side of the second surface 26 into contact with the first surface 24 at its left extreme as shown by the curve labelled "H" in FIG. 5b. With $V_1$ increased further still to 15 volts (q=1300 N-m$^{-2}$) the slope of the second surface 26 at its left extreme becomes zero as shown in the curve labelled "I". Furthermore, the area of contact between the right-hand side of the second surface 26 and the first surface 24 is increased considerably as can be seen by comparing curve "I" with the vertical dashed line in FIG. 5b which indicates the midpoint of the friction pad 18 and also the location of hinge 20. Further increases in the voltage, $V_1$, urge the surfaces 24 and 26 into more intimate contact and reduce the non-contacting distances $a_1$ and $a_2$ as shown by curve "J" in FIG. 5b. For $V_1$=30 volts (q=5100 N-m$^{-2}$), $a_1$ is decreased to 49 μm, and $a_2$ is reduced to about 14 μm.

In FIG. 5b, the lower horizontal dashed line indicates the theoretical location of the first surface 24 assuming a perfectly smooth surface. The upper horizontal dashed line in FIG. 5b indicates an upper extent of a first surface 24 due to asperities when the rms surface roughness of an as-deposited polysilicon layer is taken into account using atomic force microscopy measurements. Here, the polysilicon layer is the Poly-0 layer 32 from which the first surface 24 is formed in the first embodiment of the present invention in FIGS. 1a–1c. The rms surface roughness of the as-deposited Poly-0 layer 32 is typically 2 nanometers as indicated by the upper horizontal dashed line in FIG. 5b. At $V_1$=30 volts, the variation in the deflection, -w(x), along the length of the second surface 26 is reduced to less than the typical 2-nm rms surface roughness of the first surface 24 according to the simplified beam model of FIGS. 4a and 4b. Thus, for curve "J" in FIG. 5b, any bowing of the second surface 26 is less than about 1 nanometer so that the vertically-directed force, q=5100 N-m$^{-2}$ is nearly uniformly distributed over the entire second surface 26 of the friction pad 18.

In a second simulation of the friction test apparatus 10 of FIGS. 1a–1c, the effect of the downward force, $P_d$, on the deflection, w(x), for the driver beam 14 and the second surface 26 is calculated for a vertically-directed force of q=5100 N-m$^{-2}$ which provides a large area of contact between the first and second surfaces, 24 and 26. The dimensions of the driver beam 14 and the friction pad 18 for this simulation are unchanged from the previous simulation in FIGS. 5a and 5b. The results of this second simulation are presented in FIGS. 6a and 6b.

Figure 6A:
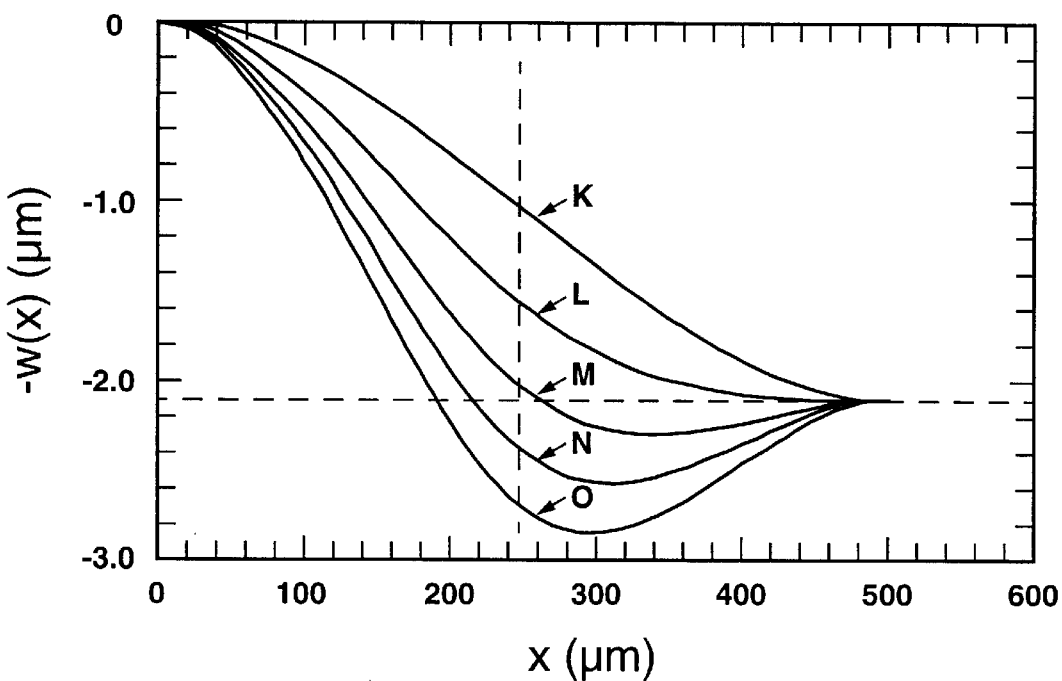
FIGS. 6a and 6b show simulations of the first embodiment of the friction test apparatus using the simplified beam model of FIGS. 4a and 4b with a variable electrostatic force applied to the driver beam, and with a fixed electrostatic force applied to the friction pad.

FIG. 6a shows calculated curves of the negative of the deflection, -w(x), plotted over the length of the driver beam 14 for various values of the downward force, $P_d$, applied as a point load at the midpoint of the driver beam 14 to simulate the behavior of the friction test apparatus 10. In an actual device 10, where the downward force, $P_d$, is distributed over the length of the driver beam 14 rather than as a point load, deflection curves similar to those of FIG. 6a can be generated using a second applied voltage, $V_2$, that is generally in the range from 0 volts up to about 60 volts. In the simulations of FIG. 6a, the deflection for the driver beam 14 in the absence of any point loading is shown by the curve labelled "K". As the point loading on the driver beam 14 is increased, the deflection, w(x), of the driver beam 14 further increases. In FIG. 6a, the curve labelled "L" corresponds to a point loading of $P_d$=90 milliNewtons per meter (mN-m$^{-1}$); the curve labelled "M" corresponds to a point loading of $P_d$=170 mN-m$^{-1}$; the curve labelled "N" corresponds to a point loading of $P_d$=230 mN-m$^{-1}$; and the curve labelled "O" corresponds to a point loading of $P_d$=284 mN-m$^{-1}$.

In this model, a maximum deflection, $w(L_d/2)$, at the midpoint of the driver beam 14 is determined by the onset of a destructive electrostatic instability which can occur when the spacing between the lower and upper central electrodes, 44 and 46, of the second electrostatic actuator is reduced to less than two-thirds of their as-fabricated or rest spacing in the absence of any applied voltages, $V_1$ or $V_2$. For the simulated device 10 of FIG. 6a, the maximum deflection, $w(L_d/2)$, is 2.7 μm which occurs for the point loading of $P_d$=284 mn-m$^{-1}$ and corresponds to curve "O". This maximum deflection to prevent a destructive electrostatic instability can thus limit the total slip distance, Δ, of the friction test apparatus 10 unless the electrodes are designed to prevent the occurrence of a short-circuit as will be described hereinafter.

Figure 6B:
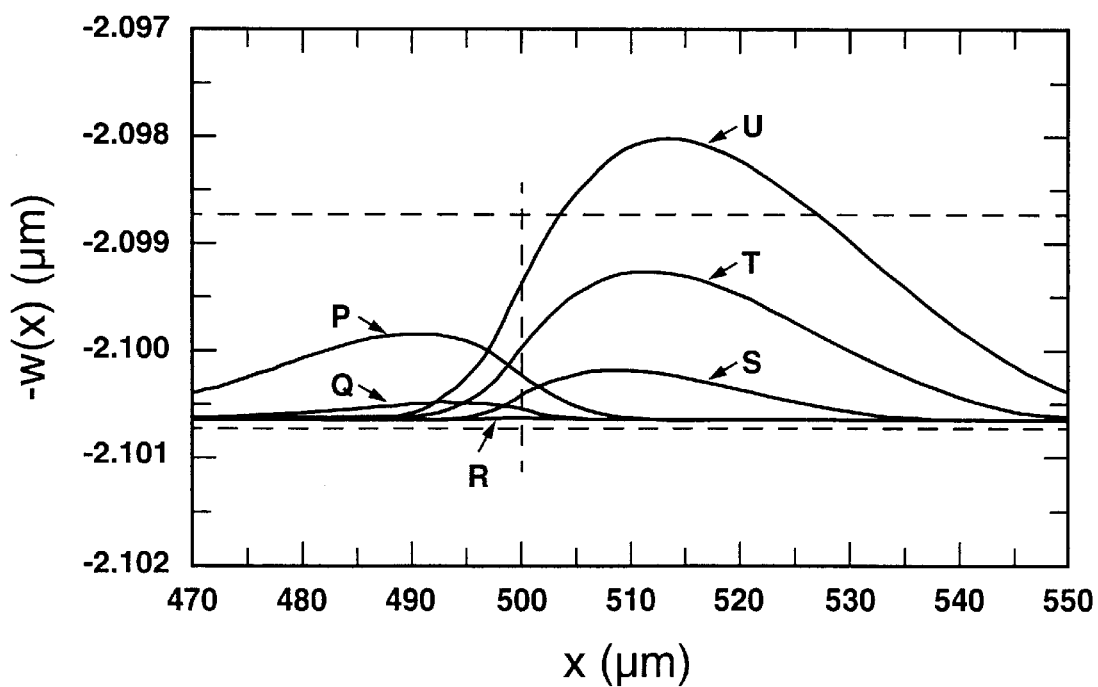

For a change in $P_d$ from 0 to 284 mN-m$^{-1}$, the slip distance, Δ, varies by about 13 nanometers for the simulated device 10 of FIGS. 6a and 6b. Over this range of slip, a normal load, N, applied to the friction pad 18 due to the combination of the vertically-directed force (q=5100 N-m$^{-2}$) and the variable driver beam loading ($0 \leq P_d \leq 284$ mN-m$^{-1}$) remains substantially constant, varying by less than 5 percent. This is due to the domination of the normal load, N, by the vertically-applied force, q.

FIG. 6b shows on an expanded horizontal scale the calculated behavior of the second surface 26 of the friction pad 18 for the various applied point loadings, $P_d$, of FIG. 6a with a fixed vertically-directed force q=5100 N-m$^{-2}$ applied to the friction pad 18. In FIG. 6b, the curve labelled "P" corresponds to the shape of the second surface 26 without any point loading of the driver beam 14 (i.e. $P_d$=0 mN-m$^{-1}$); the curve labelled "Q" corresponds to a point loading of $P_d$=50 mN-m$^{-1}$ of the driver beam 14; the curve labelled "R" corresponds to a point loading Of $P_d$=90 mN-m$^{-1}$ of the driver beam 14; the curve labelled "S" corresponds to a point loading of $P_d$=170 90 mn-m$^{-1}$ of the driver beam 14; the curve labelled "T" corresponds to a point loading of $P_d$=230 mN-m$^{-1}$ of the driver beam 14; and the curve labelled "U" corresponds to a point loading of $P_d$=284 mN-m$^{-1}$ of the driver beam 14. In FIG. 6b, the midpoint of the friction pad 18 is indicated by the vertical dashed line.

A comparison of the calculated curves of FIG. 6b with the simplified beam model of FIGS. 4a and 4b shows that $a_1$ is greater than $a_2$ for $P_d$<90 mN-m$^{-1}$ thus indicating a positive (i.e. clockwise) effective moment, $M_h$, about the connection point between the friction pad 18 and the driver beam 14 at $x=L_d$=500 μm. At $P_d$=90 mN-m$^{-1}$, the moment, $M_h$, effectively vanishes and the contact between the first and second surfaces, 24 and 26, is maximized (i.e. $a_1$=$a_2$=0). For $P_d$>90 mN-m$^{-1}$, $a_1$ is less than $a_2$ thereby indicating a negative (i.e. counterclockwise) effective moment, $M_h$.

In the simulations of FIG. 6b, the deflection in the second surface 26 of the friction pad 18 is less than the 2-nm rms surface roughness of the first surface 24 of the contact pad 22 as indicated by the upper horizontal dashed line. Thus, as $P_d$ is changed to effect lateral motion of the friction pad 18, there is expected to be little change in the force of contact between the first and second surfaces, 24 and 26. To further limit any modulation of the force of contact between the first and second surfaces, 24 and 26, the length of the friction pad 18 can be increased from the 200 μm used for these simulations up to, for example, 600 μm.

The horizontally-directed force, $F_h$, which the driver beam 14 must generate to cause slip of the friction pad 18 is the product of the coefficient of friction, μ, and the normal load, N. Although, the slip distance, Δ, which can be generated by the friction test apparatus 10 is small, the driver beam 14 can develop a substantial horizontally-directed force, $F_h$, on the order of several milliNewtons. Thus, the friction test apparatus 10 can be used to characterize contacting surfaces on a microscopic scale over a wide range of values of the coefficient of friction, μ, and over a wide range of normal loads, N.

Testing with the apparatus 10 is typically done in air (relative humidity of ~30–50%) and at room temperature. The voltages, $V_1$ and $V_2$, can be applied to probe or bonding pads (not shown) on the substrate 12 to operate the apparatus 10. In use, the friction test apparatus 10 can determine the coefficient of friction, μ, between two contacting surfaces formed of the same or different materials by applying the first and second voltages, $V_1$ and $V_2$, to the device 10 to generate determinable values of the horizontally-directed force, $F_h$, and the normal load, N. The coefficient of friction, $\mu$, can then be calculated from:

$$\mu = \frac{F_h}{N}$$

The coefficient of friction, $\mu$, can thus be determined over a wide range of values of the normal force, N, and under both static and dynamic friction conditions.

Static friction measurements can be performed by applying the first voltage, $V_1$, to the first electrostatic actuator 36 (i.e. across the stationary and moveable electrodes, 38 and 40) to generate a predetermined normal load, N, which is approximately equal to the vertically-directed force, q. Then the second voltage, $V_2$, can be applied to the second electrostatic actuator (i.e. across the central electrodes 44 and 46) and monotonically increased until the horizontally-directed force, $F_h$, reaches a critical value at which the contacting first and second surfaces, 24 and 26, slip. Applying the above equation, the coefficient of friction, $\mu$, can then be calculated.

Figure 7A:
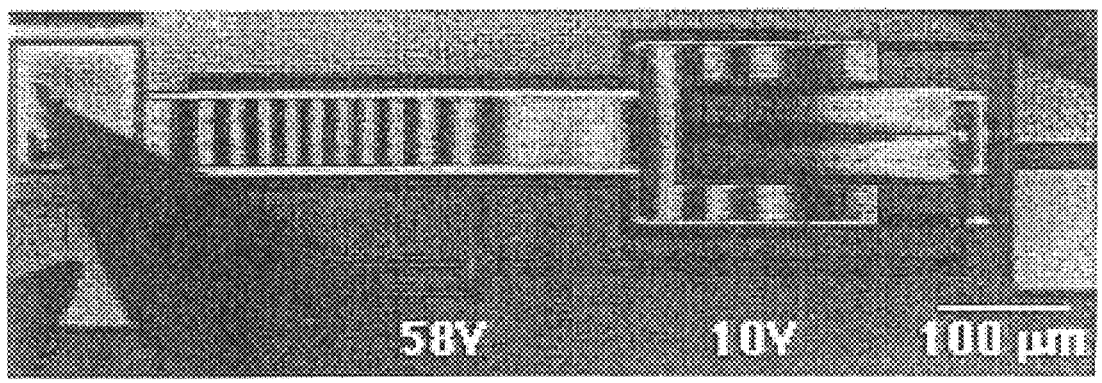
FIGS. 7a and 7b show interferograms of the first embodiment of the friction test apparatus under different operating conditions.
Figure 7B:
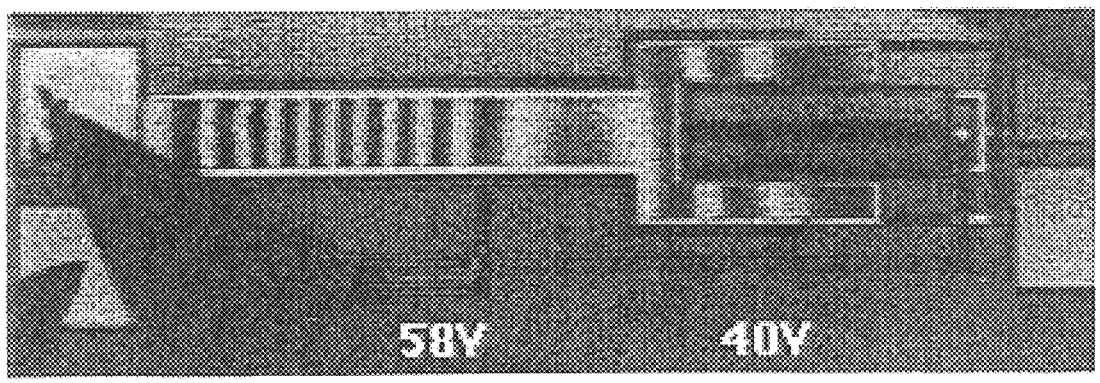

For static friction measurements, the deflection, w(x), of the driver beam 14 can be determined by interferometry as shown in FIGS. 7a and 7b. This can be done by viewing the driver beam 14 with an interferometric microscope using a particular wavelength of monochromatic light (e.g. green light at 547 nanometers wavelength from a filtered mercury light source). In FIGS. 7a and 7b, a plurality of light and dark interference fringes are produced by the monochromatic light, with each additional fringe indicating an upward or downward deflection of the driver beam 14 by a distance equal to one-half wavelength ($\lambda/2$) of the monochromatic light. Alternately, the monochromatic light can be from a laser (e.g. a helium-neon laser).

FIG. 7a shows an interferogram of the friction test apparatus 10 with $V_1$=10 volts and $V_2$=58 volts. In this interferogram, eleven dark fringes are visible counting from the square support post 16 on the left-hand side of the photograph to a broad light-colored region near the midpoint of the driver beam 14 which indicates a maximum deflection of the downward-bowed driver beam 14. In FIG. 7b, with $V_1$–40 volts and $V_2$=58 volts, only ten fringes are visible in the interferogram over the same region of the driver beam 14, thereby indicating that with this higher voltage applied to the friction pad 18, there is less slippage between the first and second surfaces, 24 and 26, for a larger value of the vertically-directed force, q.

Figure 8:
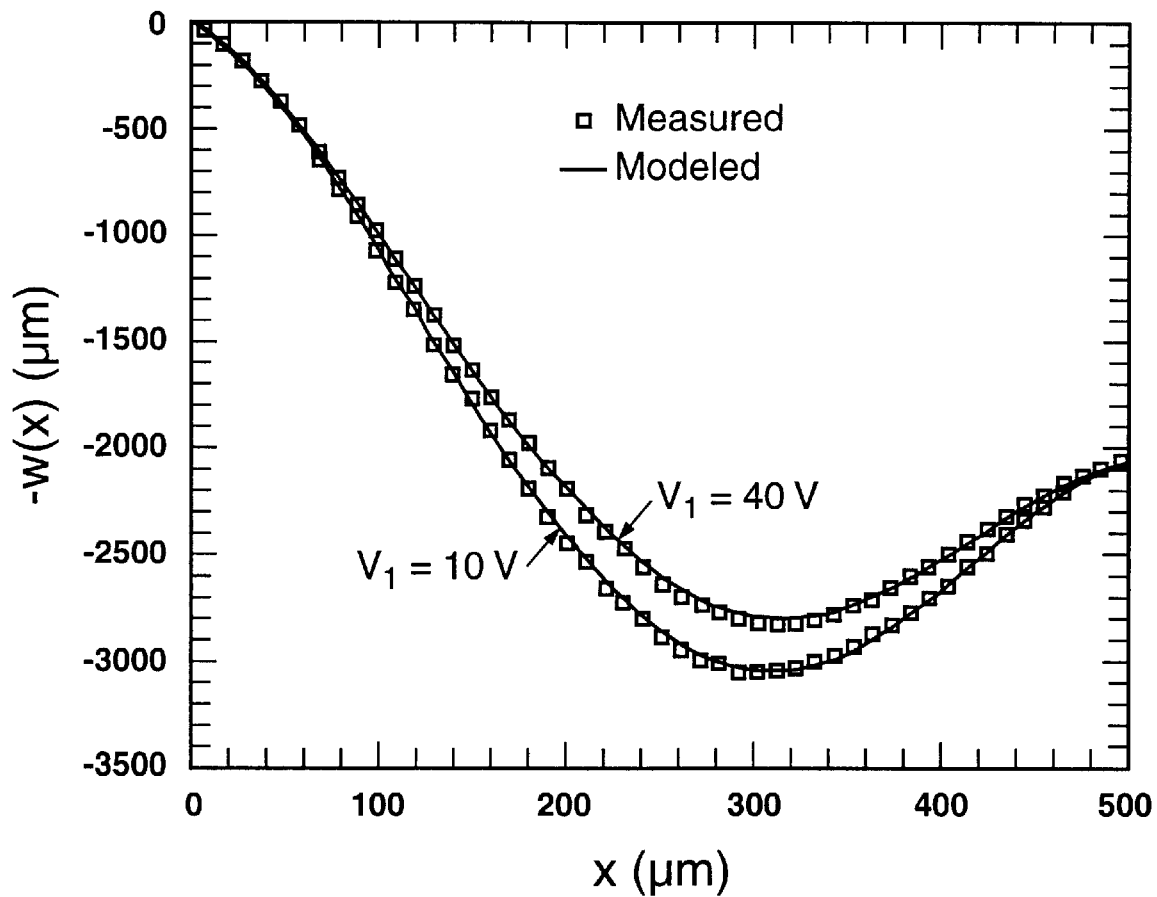
FIG. 8 shows the deflection of the driver beam under the conditions of FIGS. 7a and 7b as measured from the interferograms (square data points), and as calculated from a nonlinear finite element beam model (solid-line curves).

To further quantify the deflection, w(x), and thereby determine the slip distance, $\Delta$, for static friction measurements, a linescan can be made along the length of the driver beam 14 for each interferogram. The linescan can be obtained using a video processor to process a line of video output from a charge-coupled device (CCD) camera mounted on the microscope to record each interferogram. The linescan precisely records the position of each light and dark fringe so that the fringe positions can be used to calculate the spatial dependence of w(x) along the length of the driver beam 14. FIG. 8 shows the results from the interferograms of FIGS. 7a and 7b, with positional data determined from the linescan measurements indicated as the square data points.

In FIG. 8, the results of a nonlinear finite element beam model are also shown as solid-line curves. The nonlinear finite element beam model was used to numerically calculate the deflection, –w(x), of the driver beam 14 taking into account a charge redistribution along the length of the driver beam 14 upon deflection. This model further used a nonlinear deformation-dependent capacitive loading, including a fringing field correction, to accurately model the distributed electrostatic force due to the second applied voltage, $V_2$. Finally, to obtain reasonable agreement with the measurement data, the compliance of the support post 16 and the hinge 20 could not be ignored. Rather than estimating this compliance from the geometric structure, the slope near the extremes of the driver beam 14 was measured and included in the boundary conditions for the nonlinear model. By fitting the measured data with the finite element model, the slip distance, $\Delta$, and coefficient of friction, $\mu$, can be inferred from the interferograms. For the applied voltages, $V_1$ and $V_2$, set forth in FIGS. 7a and 7b and FIGS. 8a and 8b, a difference in the slip distance, $\Delta$, was determined to be about 5 nanometers, and the coefficient of friction was determined to be $\mu$=8.

Dynamic friction can also be measured with the apparatus 10 as a function of the velocity of movement of the friction pad 18 laterally along the contact pad 22. This can be done by applying a dc first voltage, $V_1$, to generate a predetermined normal load, N, as described previously. An alternating-current (ac) voltage, $V_2$, can then be applied to the second electrostatic actuator to move the second surface 26 across the first surface 24 at a predetermined rate or frequency for determining the coefficient of friction, $\mu$, under dynamic conditions. The term "alternating-current voltage" as used herein is defined to be a cyclic voltage with a waveform of arbitrary shape (e.g. sinusoidal, or ramped).

Figure 9:
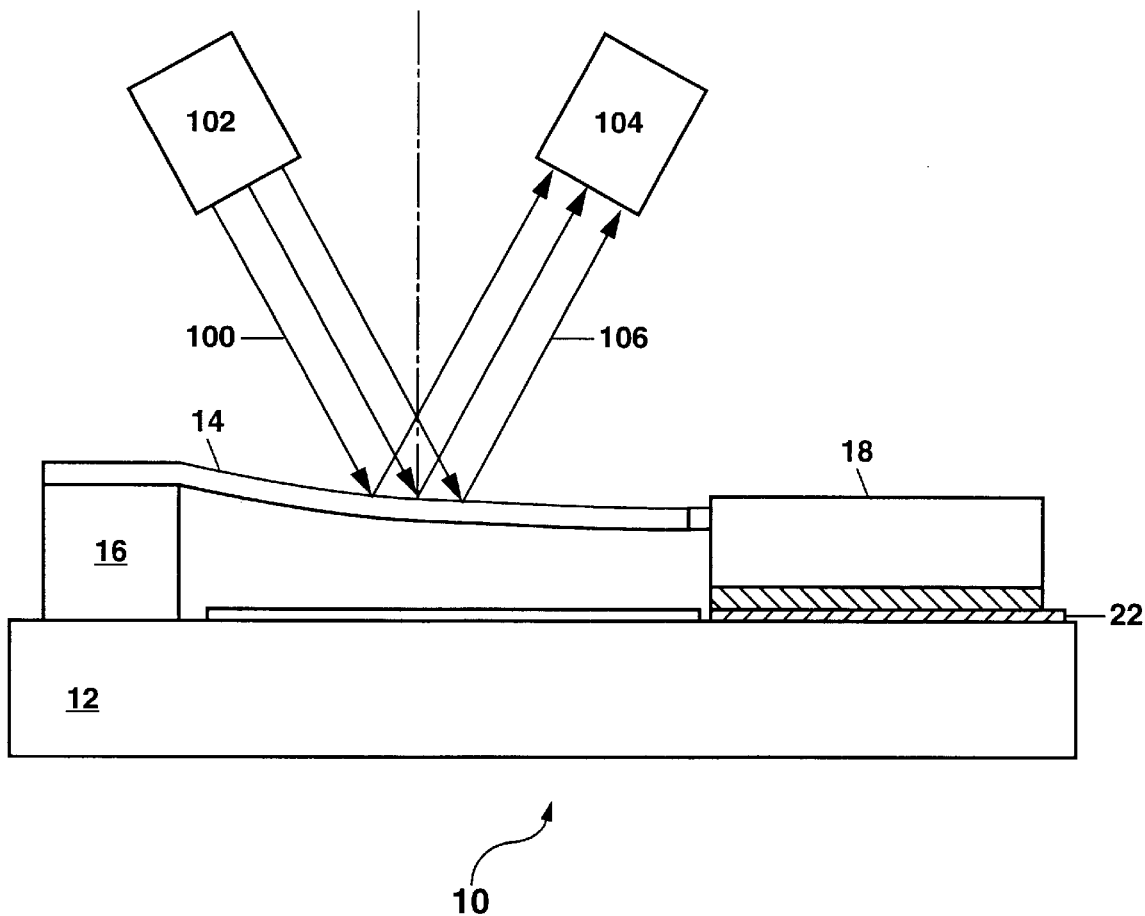
FIG. 9 schematically illustrates how the deflection of the driver beam in the first embodiment of the friction test apparatus can be determined optically by bouncing a light beam off the driver beam.

To determine the variation in the deflection, w(x) over time for dynamic friction measurements, a focused light beam 100 from a laser 102 can be directed onto a top surface of the driver beam 14 at an angle and reflected (i.e. bounced) off the driver beam 14 to a position-sensing photodetector 104. This optical detection scheme for determining the deflection of the driver beam is shown schematically in FIG. 9. As the driver beam 14 bends upon application of the ac voltage, $V_2$, the position of reflected light rays 106 from the incident light beam 100 will change. These changes can be sensed by the position-sensing detector 104 which can comprise a continuous position-sensing light detector (e.g. a Model SL-15 detector manufactured by United Detector Technology, Inc.), or alternately a plurality of light detecting elements in the form of a 1-dimensional or 2-dimensional array. An electrical output signal from the position-sensing detector 104 can be processed to recover information from which the shape of the driver beam 14 can be determined at any point in time. The recovered information can then be used to determine the coefficient of friction, $\mu$, and slip of the contacting surfaces under dynamic conditions. Measurements can be made at different frequencies of the ac voltage, $V_2$, to determine frictional parameters as a function of the velocity of movement (i.e. slip) of the second surface 26 relative to the first surface 24. The resonant frequency of the friction test apparatus of FIGS. 1a–1c is on the order of 50 kHz, thereby allowing measurements to be made up to relatively high frequencies of the ac voltage, $V_2$. This allows measurements to be made over a large frequency and velocity range free from interference due to resonance effects. This provides an advantage over the use of a comb-drive structure which has a much lower resonant frequency on the order of 3 kHz.

Furthermore, by plotting the detector output signal against the ac voltage, $V_2$, on an oscilloscope or transient data recorder, frictional losses arising from a rubbing of the friction pad 18 against the contact pad 22 can be determined at different frequencies up to about 50 kHz since these frictional losses, if present, will appear as a hysteresis loop.

The area of the hysteresis loop is proportional to the loss per cycle of the relative movement between the first and second surfaces, 24 and 26, as disclosed in an article by James M. Redmond, Maarten P. de Boer and Terry A. Michalske entitled "Integrated Modeling and Testing of a Micro Hinged Structure for Sliding Friction Measurement" (presented at the ASME International Mechanical Engineering Congress and Exposition, Anaheim, Calif., Nov. 18, 1998) which is incorporated herein by reference.

Additionally, the friction test apparatus 10 can be used to measure a force or energy of adhesion (also termed autoadhesion or stiction) between the friction pad 18 and the contact pad 22. Stiction is of particular concern for MEM devices whenever surfaces come into contact during operation of the devices. To measure stiction with the friction test apparatus 10, the first voltage, $V_1$, can be applied to bring the second surface 26 of the friction pad 18 into contact with the first surface 24 of the contact pad 22. In the absence of stiction, the second surface 26 will smoothly move away from the first surface 24 upon reducing the first voltage, $V_1$ below a certain level, or removing $V_1$ completely. If stiction occurs between the two contacting surfaces, 24 and 26, there will be an abrupt movement of the second surface 26 away from the first surface 24 as the first voltage, $V_1$, is reduced sufficiently to overcome the force of adhesion. The voltage, $V_1$, at which this occurs can then be used to determine the force of adhesion.

A more accurate measure of adhesion can be achieved with the apparatus 10 by determining the deflection, w(x), of the driver beam 14 and fitting this with the nonlinear finite element beam model described previously. This allows the force or energy of adhesion to be determined from first principles by taking into account the various forces acting upon the contact pad 18 and the driver beam 14. This method is useful even when the friction pad 18 does not release from the contact pad 22 upon removal of the first applied voltage, $V_1$.

The friction test apparatus 10 can also be used to assess the performance of particular molecular coatings for application to one or both of the surfaces, 24 and 26, to prevent or reduce stiction. Such molecular coatings are important for stiction control in MEM devices. Additionally, the apparatus 10 can be used to correlate stiction with surface roughness, or with different contacting materials (e.g. polysilicon silicon nitride, dielectrics, metals and metal alloys). Finally, the friction test apparatus can be used to correlate adhesion with wear produced by rubbing of the first and second surfaces, 24 and 26, together repeatedly.

The friction test apparatus 10 can be formed as a test structure on a wafer alongside one or more MEM devices being fabricated on the wafer. Here, the area of the apparatus 10 can be small (on the order of 100 μm×1000 μm) to conserve space on the wafer, thereby allowing more room for the other MEM devices. Measurements with the apparatus 10 can then be used to assess a production yield of the MEM devices or as an in situ diagnostic tool for evaluating the quality of the device processing.

Critical properties such as friction are highly sensitive to surface conditions which are difficult to monitor and control during device processing. The friction test apparatus 10 will allow such surface conditions to be determined from friction measurements in order to provide information to improve process control and quality. By distributing a plurality of friction test devices 10 across a wafer, the production uniformity across the wafer can be determined. The friction test apparatus 10 can further provide useful information about wafer to wafer process variations and about lot to lot uniformity. Additionally, dynamic measurements with the friction test apparatus 10 can be used to simulate wear between contacting surfaces in the MEM devices with or without stiction-reducing coatings, and to assess the reliability of the MEM devices after repeated operation.

Figure 10A:
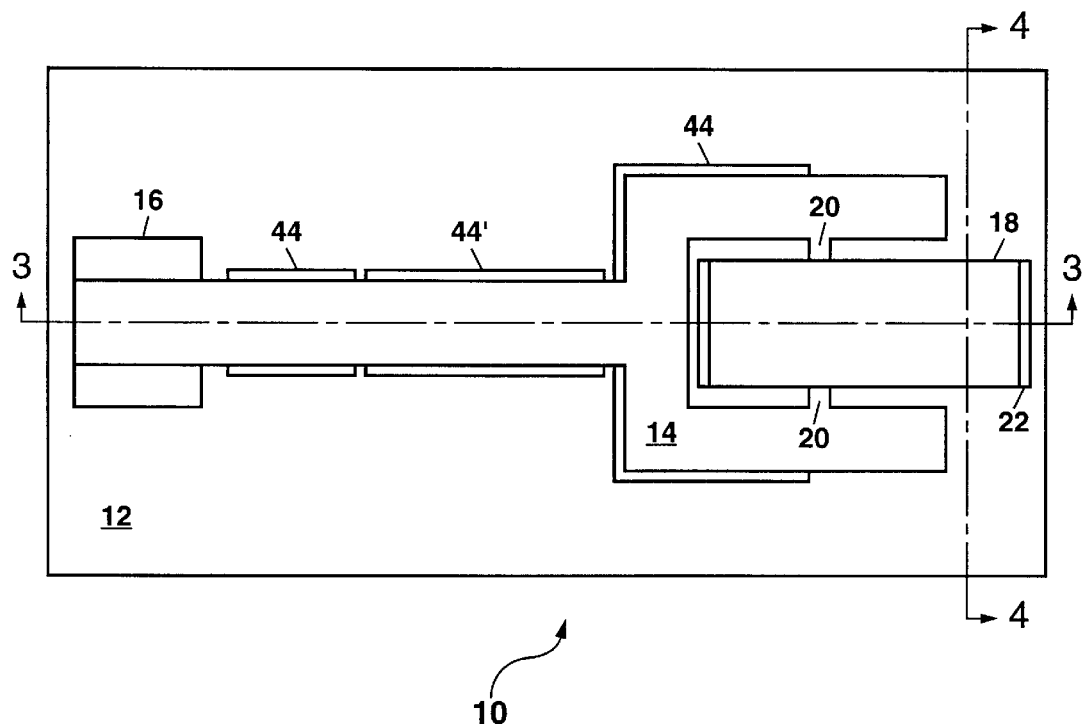
FIG. 10a shows a schematic plan view of a second embodiment of the MEM friction test apparatus of the present invention.
Figure 10B:
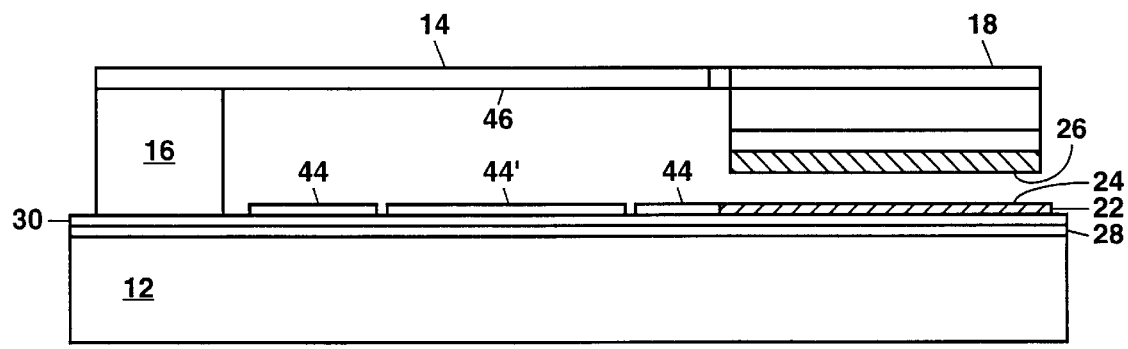
FIG. 10b shows a schematic cross-section view of the second embodiment of the MEM friction test apparatus along the line 3—3.
Figure 10C:
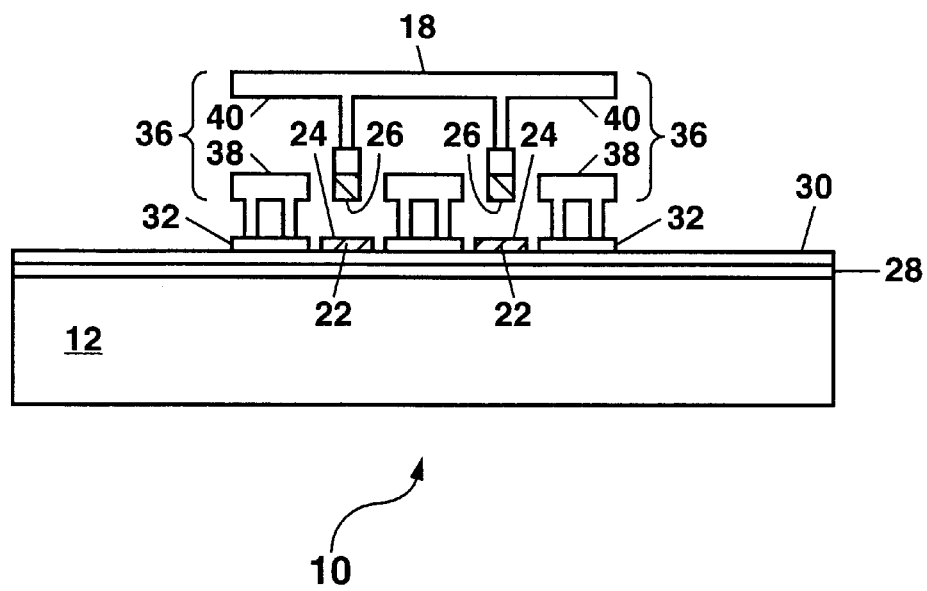
FIG. 10c shows a slightly enlarged schematic cross-section view of the second embodiment of the MEM friction test apparatus along the line 4—4.
Figure 11A:
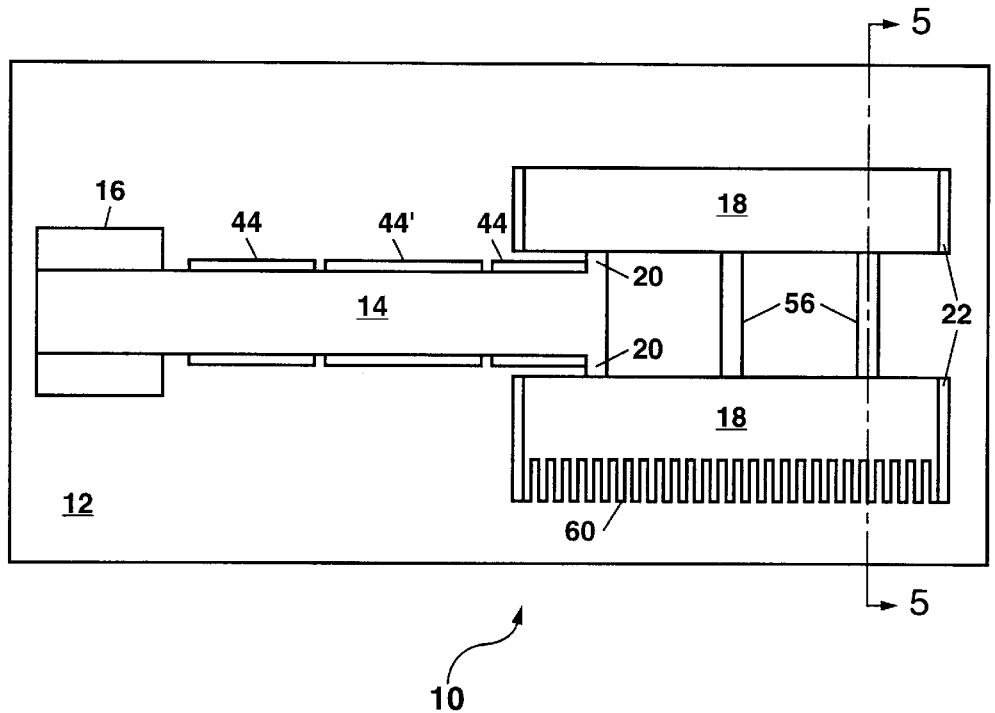
FIG. 11a shows a schematic plan view of a third embodiment of the MEM friction test apparatus of the present invention.
Figure 11B:
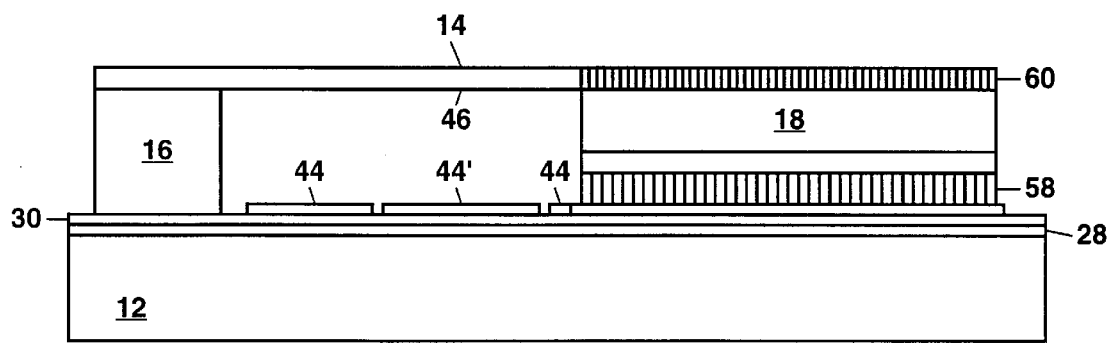
FIG. 11b shows a schematic side view of the third embodiment of the MEM friction test apparatus.
Figure 11C:
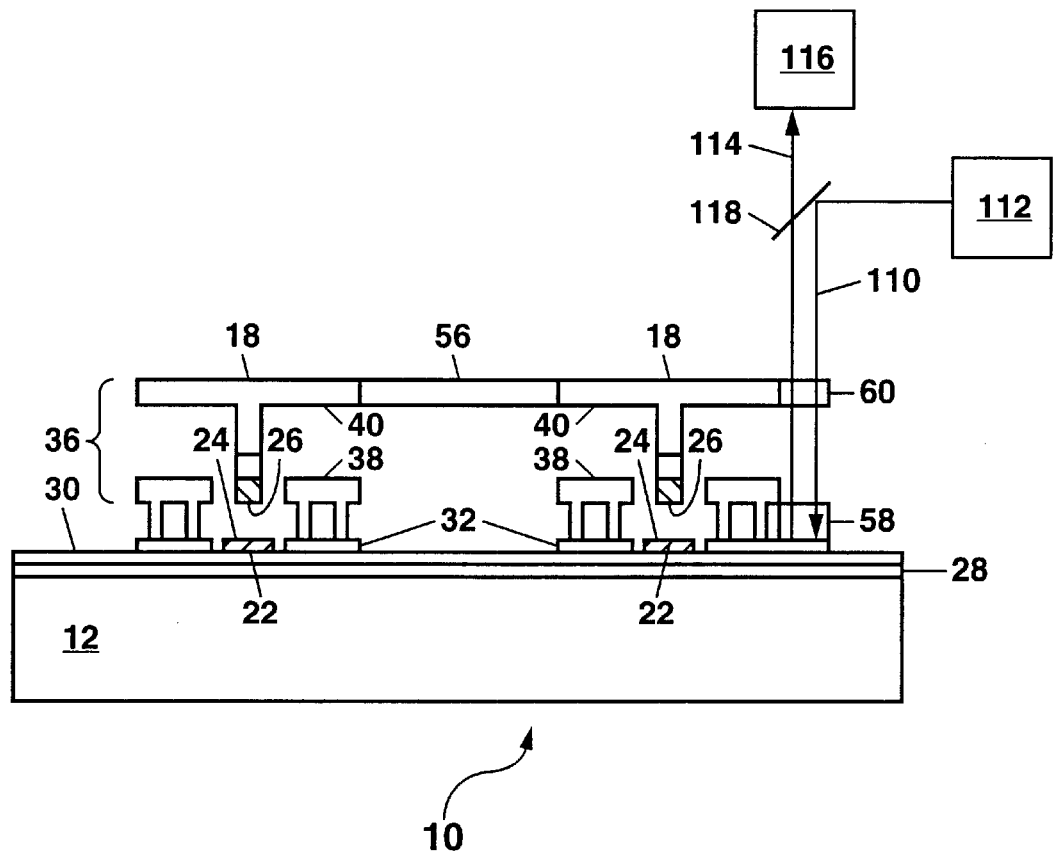
FIG. 11c shows a slightly enlarged schematic cross-section view of the third embodiment of the MEM friction test apparatus along the line 5—5, and further shows an optical detection scheme employing a pair of diffraction gratings of different periodicity that can be used to accurately measure lateral movement of the friction pad.

Other embodiments of the friction test apparatus 10 are possible according to the teachings of the present invention. A second embodiment of the present invention is shown in FIGS. 10a–10c; and a third embodiment of the present invention is shown in FIGS. 11a–11c. These further embodiments of the friction test apparatus 10 can be formed by conventional surface micromachining processes similar to those described previously with reference to FIGS. 2a–2o.

The second embodiment of the friction test apparatus 10 is similar to the first embodiment described heretofore, but differs primarily in the design of the friction pad 18 and the contact pad 22, each of which have two surfaces 24 or 26. Additionally, the first electrostatic actuator 36 comprises three stationary electrodes 38 and three moveable electrodes 40. In the second embodiment of the friction test apparatus 10, the lower central electrode 44 is segmented with a central portion 44' near the midpoint of the driver beam 14 being held at ground potential so that the voltage, $V_2$, is applied between the driver beam 14 and segments of the electrode 44 that are superposed below either end of the driver beam 14 (see FIGS. 10a and 10b). This segmented electrode arrangement allows a greater deflection of the driver beam 14 without the danger of shorting out the lower and upper central electrodes, 44 and 46. Additionally, a threshold voltage for an electrostatic instability is increased to higher values of $V_2$ in this second embodiment. This allows an increased deflection of the driver beam 14 before onset of the electrostatic instability, thereby providing a greater slip distance, Δ, for the friction pad 18. Simulations using the nonlinear finite element beam model show that Δ can reach about 50 nanometers in the second embodiment of the present invention.

The second embodiment of the friction test apparatus 10 further provides a more stable configuration for the contacting surfaces, 24 and 26, to overcome a torsional moment about a longitudinal axis of the friction pad 18 which can occur if the electrostatic force generated by the electrodes 38 and 40 is unbalanced. In this second embodiment of the friction test apparatus 10, the areas of the second surface 26 and the areas and spacing of the electrodes 38 and 40 can be adjusted to provide a predetermined range for the vertically-directed force, q. Additionally, the areas of the forked driver beam 14 and superposed lower central electrode 44 can be adjusted to provide a predetermined range for the horizontally-directed force, $F_h$. Finally, the location of the hinges 20 is important for optimum contacting of the first and second surfaces, 24 and 26, and can be determined for particular lengths of the driver beam 14 and the friction pad 18 by use of the simplified beam model described herein.

A third embodiment of the friction test apparatus 10 of the present invention is shown schematically in FIGS. 11a–11c. The third embodiment of the apparatus 10 includes a pair of friction pads 18 joined by a plurality of cross-members 56 and suspended on an elongate cantilevered driver beam 14 by a pair of attachment hinges 20. Each friction pad 18 includes a pair of stationary electrodes 38 and a pair of moveable electrodes 40 to form the first electrostatic actuator 36 for bringing a second surface 26 of the friction pad 18 into contact with a first surface of a contact pad 22 with a predetermined level of contacting force (see FIG. 11c). A second electrostatic actuator is formed by an upper central electrode 46 formed on or within the driver beam 14 and a lower central electrode 44 formed on the substrate 12 superposed below the driver beam 14. The lower central electrode 44 is segmented as described previously with reference to FIGS. 10a and 10b to provide an increased range of slip, Δ.

In this embodiment of the present invention, a different or additional optical detection scheme can be used for accurately measuring lateral movement of the friction pads 18 using a stationary diffraction grating 58 formed on the substrate 12 and a moveable diffraction grating 60 is formed on one of the friction pads 18, thereby forming a Moiré interferometer. These diffraction gratings preferably have slightly different grating periods (e.g. 2.000 and 2.025 $\mu$m) and can be used to accurately determine movement of the friction pads 18 (i.e. the slip distance, Δ).

The optical detection scheme uses an incident light beam 110 from a source 112 (e.g. a lamp, laser, or light-emitting diode) that is directed downward through each of the diffraction gratings, 58 and 60, with a reflected or scattered return component 114 of the incident light being detected with a photodetector 116, or alternately with a CCD camera. Optics including a beamsplitter 118 and focusing lens (not shown) that are used to direct the incident light 110 and the return component 114 can be a part of a microscope (not shown).

Light rays in the incident and reflected light interfere constructively and destructively. depending on whether the light rays interact with one or both of the diffraction gratings, 58 and 60. Visually, this position-dependent interference of the light rays due to the slight difference in the grating periods appears as an interference pattern (i.e. a Moiré pattern). Upon the slightest motion of the friction pad 18, the interference pattern shifts due to a change in overlap of the gratings, 58 and 60, which have different grating periods. This allows a very sensitive detection of any motion of the friction pad 18 along its longitudinal axis with a positional accuracy that can be on the order of 1–10 nanometers (i.e. much smaller than the wavelength of the light). The periodicity of each diffraction grating will, in general, depend upon fabrication tolerances of the apparatus 10 and can be, for example, in the range of 1–5 $\mu$m.

Other applications and variations of the present invention will become evident to those skilled in the art. For example, although the present invention has been described as a polysilicon micromachined structure with a sacrificial material that can be removed by selecting etching with an HF-based etchant, the test structure 10 could also be formed as a silicon dioxide structure with a sacrificial material comprising polysilicon for removal by a silicon-specific selective etchant. Furthermore, although the present invention has been described as a MEM device, the test structure 10 can also be formed on a millimeter-size scale for application to millielectromechanical devices (i.e. millimachines). Finally, although the substrate 12 generally comprises silicon, other embodiments of the present invention can be formed with other types of substrates (e.g. glass, alumina, a metal or metal alloy). The actual scope of the invention is intended to be defined in the following claims when viewed in their proper perspective based on the prior art.

What is claimed is:

1. A friction test apparatus formed on a substrate, comprising:
   (a) a first surface formed above the substrate;
   (b) a second surface formed on an elongate friction pad suspended above the substrate over the first surface and moveable into contact with the first surface, the second surface being substantially planar and further being laterally moveable along a longitudinal axis of the first surface, thereby rubbing against the first surface;
   (c) means for providing an adjustable vertically-directed force to bring the second surface into contact with the first surface; and
   (d) a moveable driver beam upon which the friction pad is suspended for providing an adjustable horizontally-directed force to effect lateral movement of the second surface relative to the first surface, with the moveable driver beam comprising an electrostatic actuator further comprising an upper central electrode located on the driver beam and a lower central electrode formed above the substrate and superposed below the upper central electrode.

2. The apparatus of claim 1 further comprising means for determining the lateral movement of the second surface relative to the first surface, thereby providing, in combination with the vertically- and horizontally-directed forces, a measure of friction between the first and second surfaces.

3. The apparatus of claim 2 wherein the means for determining the lateral movement comprises an optical interferometer.

4. The apparatus of claim 2 wherein the means for determining the lateral movement comprises a light beam bounced off an upper surface of a driver beam whereon the friction pad is suspended.

5. The apparatus of claim 4 wherein the means for determining the lateral movement further comprises a position-sensing detector for sensing the light beam bounced off the upper surface of the driver beam.

6. The apparatus of claim 2 wherein the means for determining the lateral displacement comprises a stationary diffraction grating on the substrate, and a moveable diffraction grating formed on a driver beam whereon the friction pad is suspended, with the moveable diffraction grating being positioned above the stationary diffraction grating and in substantial alignment therewith.

7. The apparatus of claim 6 wherein the stationary and moveable diffraction gratings have different grating periods.

8. The apparatus of claim 1 wherein at least one of the first and second surfaces comprises a material selected from the group consisting of polycrystalline silicon, silicon nitride, dielectrics, metals and metal alloys.

9. The apparatus of claim 1 wherein the means for providing the vertically-directed force comprises another electrostatic actuator.

10. The apparatus of claim 9 wherein the other electrostatic actuator comprises a pair of electrodes on each side of the friction pad, with each pair of electrodes comprising a stationary electrode attached to the substrate and a moveable electrode attached to the friction pad.

11. The apparatus of claim 1 wherein one end of the driver beam is attached to a support post formed on the substrate, and the other end of the driver beam is attached to the friction pad.

12. The apparatus of claim 11 wherein the attachment of the driver beam to the friction pad is by at least one hinge, with each hinge being offset a distance from the end of the friction pad nearest the driver beam.

13. The apparatus of claim 12 wherein the offset distance is selected to maximize an area of contact between the first and second surfaces.

14. The apparatus of claim 1 wherein the lateral movement of the second surface relative to the first surface is cyclic.

15. The apparatus of claim 1 further comprising means for determining a force or energy of adhesion between the first and second surfaces.

16. A friction test apparatus formed on a substrate and comprising:
   (a) a cantilevered driver beam supported at one end thereof above the substrate and substantially co-planar with the substrate;
   (b) an elongate friction pad connected to the other end of the driver beam by a pair of hinges attached to opposite sides of the friction pad;
   (c) a contact pad formed on the substrate below the friction pad;
   (d) a first electrostatic means for providing a vertically-directed force to bring the friction pad into mechanical contact with the contact pad; and
   (e) a second electrostatic means for providing a horizontally-directed force to move the friction pad laterally along the contact pad.

17. The apparatus of claim 16 further comprising means for determining a lateral displacement of the friction pad along the contact pad for use in calculating, in combination with the vertically- and horizontally-directed forces, a measure of friction between the friction pad and the contact pad.

18. The apparatus of claim 17 wherein the means for determining the lateral displacement comprises an optical interferometer.

19. The apparatus of claim 18 wherein the measure of friction comprises a measure of static friction.

20. The apparatus of claim 17 wherein the means for determining the lateral displacement comprises a light beam directed onto an upper surface of the driver beam at an angle and reflected off therefrom with a spatial position of the reflected light beam being sensed.

21. The apparatus of claim 20 wherein the measure of friction comprises a measure of dynamic friction.

22. The apparatus of claim 21 wherein the dynamic friction is measurable as a function of a velocity of movement of the friction pad laterally along the contact pad upon repeated actuation of the second electrostatic means with an alternating-current (ac) voltage.

23. The apparatus of claim 20 wherein repeated actuation of the second electrostatic means provides a measure of frictional loss resulting from a rubbing of the friction pad against the contact pad.

24. The apparatus of claim 17 wherein the means for determining the lateraldisplacement comprises a stationary diffraction grating on the substrate and a moveable diffraction grating formed on the driver beam above the stationary diffraction grating.

25. The apparatus of claim 24 wherein the stationary and moveable diffraction gratings have different grating periods.

26. The apparatus of claim 16 wherein at least one of the friction pad and the contact pad comprises a material selected from the group consisting of polycrystalline silicon, silicon nitride, dielectrics, metals and metal alloys.

27. The apparatus of claim 16 where the first electrostatic means comprises a pair of upper side electrodes formed on the driver beam adjacent to each side of the friction pad, and a lower side electrode formed above the substrate and superposed below each of the upper side electrodes, the side electrodes acting to move the friction pad downward in response to a first applied voltage, thereby generating the vertically-directed force to bring the friction pad into mechanical contact with the contact pad.

28. The apparatus of claim 27 wherein the vertically-directed force is adjustable.

29. The apparatus of claim 16 wherein the second electrostatic means comprises an upper central electrode on the driver beam and a lower central electrode formed above the substrate and superposed below the upper central electrode, the central electrodes acting to bend the driver beam in response to a second applied voltage, thereby generating the horizontally-directed force to move the friction pad laterally along the contact pad.

30. The apparatus of claim 16 wherein the location of the hinges attached to opposite sides of the friction pad is selected to maximize an area of contact of the friction pad with the contact pad over a range of the vertically-directed force.

31. The apparatus of claim 18 further comprising means for determining a force or energy of adhesion between the friction pad and the contact pad.

32. An apparatus for assessing friction or wear in microelectromechanical systems, comprising:
   (a) a pair of substantially planar surfaces, with one of the surfaces being stationary, and with the other surface comprising a bottom surface of an elongate friction pad which is moveable in both a vertical direction and a horizontal direction;
   (b) a first electrostatic actuator for applying a vertical-directed force to bring the surfaces into contact with each other, with the first electrostatic actuator comprising a pair of superposed electrodes on each side of the friction pad, with each pair of electrodes further comprising a stationary electrode on the substrate below a moveable electrode attached to the friction pad;
   (c) means for applying a lateral force to produce rubbing motion between the surfaces; and
   (d) means for determining a lateral displacement between the surfaces resulting from the rubbing motion.

33. The apparatus of claim 32 wherein the friction pad is suspended over the substrate at one end of a cantilevered beam.

34. The apparatus of claim 33 wherein the friction pad is attached to the cantilevered beam by at least one hinge.

35. The apparatus of claim 34 wherein the cantilevered beam is forked at the end wherein the beam is attached to the friction pad.

36. The apparatus of claim 33 wherein the means for applying the lateral force comprises a second electrostatic actuator comprising an upper central electrode on the cantilevered beam and a lower central electrode formed above the substrate and superposed below the upper central electrode.

37. The apparatus of claim 36 wherein the means for determining the lateral displacement between the surfaces comprises an optical interferometer.

38. The apparatus of claim 36 wherein the means for determining the lateral displacement between the surfaces comprises a light beam bounced off the cantilevered beam and sensed with a position-sensing detector.

39. The apparatus of claim 36 wherein the means for determining the lateral displacement between the surfaces comprises a pair of diffraction gratings, including a stationary diffraction grating located on the substrate and a moveable diffraction grating located on the cantilevered beam.

40. The apparatus of claim 39 wherein each diffraction grating of the pair has a different grating period.

41. The apparatus of claim 32 wherein the stationary surface comprises a material deposited on a substrate.

42. The apparatus of claim 32 wherein at least one of the stationary and moveable surfaces comprises a material selected from the group consisting of polycrystalline silicon, silicon nitride, dielectrics, metals and metal alloys.

43. The apparatus of claim 32 wherein the rubbing motion is cyclic.

44. A microelectromechanical (MEM) fabrication process quality tool, comprising:
(a) a micromachined cantilevered-beam structure formed on a substrate and further comprising a first substantially planar surface formed above the substrate, and a second substantially planar surface formed as a bottom surface of an elongate friction pad attached to a cantilevered beam, with the second surface being superposed over the first surface, being moveable to contact the first surface, and being moveable laterally relative to the first surface;
(b) means for applying a vertically-directed force to bring the second surface into contact with the first surface; and
(c) means for applying a horizontally-directed force to move the second surface laterally relative to the first surface, thereby enabling a determination of static or dynamic friction between the first and second surfaces.

45. The MEM fabrication process quality tool of claim 44 wherein the substrate comprises monocrystalline silicon, and the micromachined structure is formed, at least in part, from polycrystalline silicon.

46. The MEM fabrication process quality tool of claim 44 further comprising optical means for determining the lateral motion of the second surface relative to the first surface.

47. The MEM fabrication process quality tool of claim 44 wherein the means for applying a vertically-directed force comprises a first electrostatic actuator, and the means for applying the horizontally-directed force comprises a second electrostatic actuator.

48. A test structure for assessing the reliability of microelectromechanical devices, comprising a pair of substantially planar surfaces formed above a substrate, with one of the surfaces being formed on an elongate friction pad supported at one end of a cantilevered beam and being laterally moveable relative to the other surface with an adjustable force of contact for determining wear of the surfaces upon repeated movement.

49. The test structure of claim 48 wherein the adjustable force of contact is provided by a first electrostatic actuator.

50. The test structure of claim 48 wherein the lateral motion of the moveable surface is provided by an electrostatic actuator which acts to alter the length of the cantilevered beam.

51. The test structure of claim 48 wherein the substrate comprises monocrystalline silicon, and the test structure comprises, at least in part, polycrystalline silicon.

* * * * *